(12) United States Patent
Melis et al.

(10) Patent No.: US 8,802,407 B2
(45) Date of Patent: Aug. 12, 2014

(54) ISOPRENE HYDROCARBON PRODUCTION USING GENETICALLY ENGINEERED CYANOBACTERIA

(75) Inventors: Anastasios Melis, El Cerrito, CA (US); Pia Lindberg, Uppsala (SE)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/318,126

(22) PCT Filed: Apr. 30, 2010

(86) PCT No.: PCT/US2010/033240
§ 371 (c)(1),
(2), (4) Date: Jan. 17, 2012

(87) PCT Pub. No.: WO2010/127290
PCT Pub. Date: Nov. 4, 2010

(65) Prior Publication Data
US 2012/0135490 A1    May 31, 2012

Related U.S. Application Data

(60) Provisional application No. 61/174,729, filed on May 1, 2009.

(51) Int. Cl.
*C12P 5/02* (2006.01)
*C12N 9/00* (2006.01)
*C12N 1/20* (2006.01)
*C12N 1/12* (2006.01)
*C12N 15/00* (2006.01)
*C07H 21/04* (2006.01)

(52) U.S. Cl.
USPC ..... 435/167; 435/183; 435/252.3; 435/257.2; 435/320.1; 536/23.2

(58) Field of Classification Search
None
See application file for complete search history.

(56) References Cited

U.S. PATENT DOCUMENTS

2008/0038805 A1* 2/2008 Melis ............................ 435/167
2009/0280545 A1* 11/2009 Mendez et al. ............... 435/157
2011/0053216 A1* 3/2011 Vermaas ...................... 435/69.1

FOREIGN PATENT DOCUMENTS

WO    WO 2008/003078 A2    1/2008
WO    WO 2008/130437 A2    10/2008

OTHER PUBLICATIONS

International Search Report from PCT/US2010/033240, dated Jan. 24, 2011.

* cited by examiner

*Primary Examiner* — Iqbal H Chowdhury
(74) *Attorney, Agent, or Firm* — Kilpatrick Townsend & Stockton LLP

(57) ABSTRACT

The present invention provides methods and compositions for producing isoprene hydrocarbons from cyanobacteria.

16 Claims, 10 Drawing Sheets

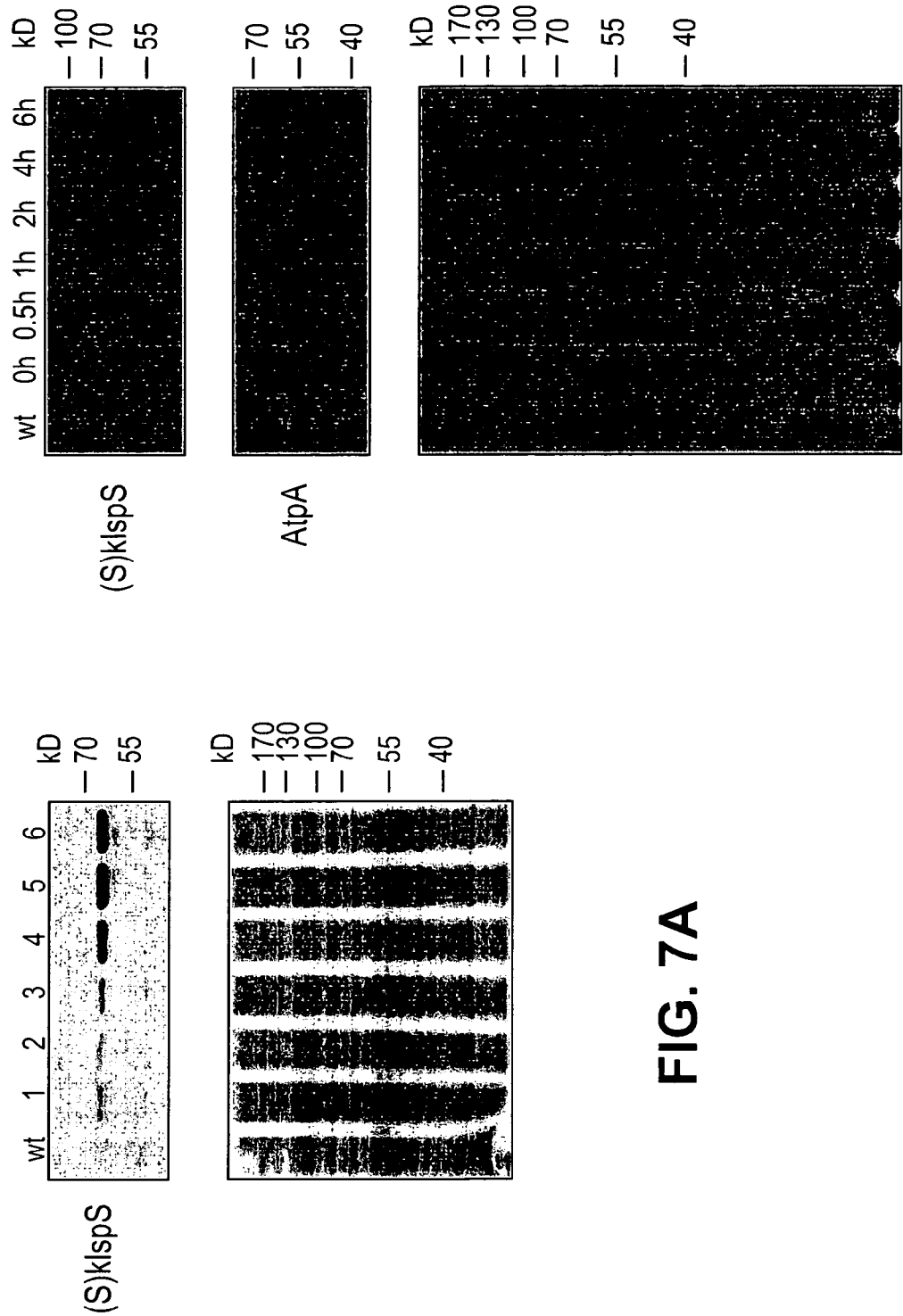

CLUSTAL W (1.83) multiple sequence alignments of known IspS proteins
The putative chloroplast transit peptide cpTP is shown by underlined sequences;
All Cys amino acids are in large, highlighted font, including conservative Ser
substitutions

```
alba         MATELIC LHRPISLTHKLFRNPLP------KVIQATPLTLKLRC SVSTENVSFTETET    52
tremuloides  MATELIC LHRPISLTHKLFRNPLP------KVIQATPLTLKLRC SVSTENVSFSETET    52
nigra        MATELIC LHRPISLTHKLFRNPLP------KVIQATPLTLKLRC SVSTENVSFTETET    52
kudzu        MATNLIC LSNKLSSPTPTPSTRFPQSKNFITQKTSLANPKPWRVIC ATSSQFTQITEHN-    59
             ****:** *:*:*:  :.           :   .  :        *      *:    :

alba         EARRSANYEPNSWDYDYLLSSDTDESIEVYKDKAKKLEAEVRREINNEKAEFLTLLELID   112
tremuloides  ETRRSANYEPNSWDYDYLLSSDTDESIEVHKDKAKKLEAEVRREINNEKAEFLTLLELID   112
nigra        ETRRSANYEPNSWDYDYLLSSDTDESIEVYKDKAKKLEAEVRREINNEKAEFLTLPELID   112
kudzu        -SRRSANYQPNLWNFEFLQSLENDLKVEKLEEKATKLEEEVR CMINRVDTQPLSLLELID   118
              :****:.*::::* *:   .  :       ::  :  :  **:* **** alba         NVQRLGLGYRFESDIRGALDRFVSSGGFDAVTKTSLHGTALSFRLLRQHGFEVSQEAFSG   172
tremuloides  NVQRLGLGYRFESDIRRALDRFVSSGGFDVTKTSLHGTALSFRLLRQHGFEVSQEAFSG   172
nigra        NVQRLGLGYRFESDIRRALDRFVSSGGFDAVTKTSLHATALSFRLLRQHGFEVSQDVFER   172
kudzu        DVQRLGLTYKFEKDIIKALENIVLLD-ENKKNKSDLHATALSFRLLRQHGFEVSQDVFER   177
             :******.*:**.**  ***:. ::.   :     **:.***************:.:.

alba         FKDQNGNFLENLKEDIKAILSLYEASFLALEGENILDEAKVFAISHLKELSEEKIGKELA   232
tremuloides  FKDQNGNFLENLKEDIKAILSLYEASFLALEGENILDEAKVFAISHLKELSEEKIGKELA   232
nigra        FKDQNGNFLKNLKEDIKAILSLYEASFLALEGENILDEAKVFAISHLKELSEEKIGKELA   232
kudzu        FKDKEGGFSGELKGDVQGLLSLYEASYLGFEGENLLEEARTFSITHLKNNLKEGINTKVA   237
             ***: *.*  :** *:: :******:*.:****:*:**  *:*:***:.*.*  *.  * alba         EQVNHALELPLHRRTQRLEAVWSIEAYRKKEDANQVLLELAILDYNMIQSVYQRDLRETS   292
tremuloides  EQVSHALELPLHRRTQRLEAVWSIEAYRKKEDANQVLLELAILDYNMIQSVYQRDLRETS   292
nigra        EQVNHALELPLHRRTQRLEAVWSIEAYRKKEDADQVLLELAILDYNMIQSVYQRDLRETS   292
kudzu        EQVSHALELPYHQRLHRLEARWFLDKYEPKEPHHQLLLELAKLDFNMVQTLHQKELQDLS   297
             ***.****** *:* :****.*   .* *:* .:::***** **:**:*:::*::   *
```

ISOPRENE HYDROCARBON PRODUCTION USING GENETICALLY ENGINEERED CYANOBACTERIA

CROSS-REFERENCE TO RELATED APPLICATIONS

This application is the U.S. National Stage entry of International Application No. PCT/US2010/033240, filed Apr. 30, 2010, which claims benefit of U.S. provisional application No. 61/174,729, filed May 1, 2009, each application is herein incorporated by reference.

STATEMENT AS TO RIGHTS TO INVENTIONS MADE UNDER FEDERALLY SPONSORED RESEARCH AND DEVELOPMENT

Not applicable.

REFERENCE TO A SEQUENCE LISTING

This application includes a Sequence Listing as a text file named "SEQTXT_79438-824391_197610US.txt" created Oct. 28, 2011 and containing 33,174 bytes. The material contained in this text file is incorporated by reference.

BACKGROUND OF THE INVENTION

Formation of isoprene in plants is due to the presence of an isoprene synthase (IspS) gene (Miller et al., *Planta* 213: 483-487, 2001), a nuclear gene encoding for a chloroplast-localized protein that catalyzes the conversion of one of the products of the MEP pathway, dimethylallyl diphosphate (DMAPP), to isoprene (Lichtenthaler, *Biochem Soc Trans* 28: 785-789, 2000). Plant isoprene synthases, encoded by the IspS gene, have been cloned and characterized from poplar (*Populus alba; Populus tremuloides*) (Miller et al. 2001, supra; Sasaki et al., *FEBS Lett* 579: 2514-2518, 2005; Sharkey et al., *Plant Physiol* 137: 700-712, 2005) and kudzu vine (*Pueraria montana*) (Sharkey et al., 2005). Isoprene is a small hydrophobic and volatile molecule that can easily go through cellular membranes and thereby be emitted from the leaves into the atmosphere. The process of heat stress-induction and emission of such short-chain volatile hydrocarbons by plants has been discussed as undesirable pollution of the atmosphere in the literature (Sharkey et al., *Ann Bot* (*Lond*) 101: 5-18, 2008). It has been shown that isoprene production and release can function as a protective mechanism for the plant via which to increase thermo-tolerance (Sasaki et al., *Plant Cell Physiol* 48: 1254-1262, 2007; Sharkey et al., *Plant Physiol* 125: 2001-2006, 2001; Singsaas et al., *Plant Physiol* 115: 1413-1420, 1997). It has also been described that volatile hydrocarbons can be produced using microalgae, cyanobacteria, or bacteria that have been engineered to express IspS genes (WO 2008/003078).

Cyanobacteria express the MEP pathway. The corresponding enzymes are involved in the biosynthesis of a variety of molecules (e.g., carotenoids, tocopherols, phytol, sterols, hormones, among many others). However, unlike certain herbaceous, deciduous and conifer plants, cyanobacteria do not have isoprene synthase.

The MEP isoprenoid biosynthetic pathway in bacteria typically uses pyruvate and glyceraldehyde-3-phosphate as substrates, which are combined to form deoxyxylulose-5-phosphate (DXP). DXP is then converted into methyl-erythitol phosphate (MEP), which is subsequently modified to form hydroxy-2-methyl-2-butenyl-4-diphosphate (HMBPP). HMBPP is the substrate required for the formation of IPP and DMAPP as the final step in this biosynthetic pathway (FIG. 1). Cyanobacteria also contain an IPP isomerase that catalyzes the inter-conversion of IPP and DMAPP (Barkley et al., *J Bacteriol* 186: 8156-8158, 2004; Poliquin et al., *J Bacteriol* 186: 4685-4693, 2004). Genetic inactivation of the IPP isomerase gene results in impairment of isoprenoid biosynthesis from photosynthetic substrates (Poliquin et al., 2004, supra).

Previous studies with *Synechocystis* sp. PCC 6803 have shown that, under photosynthetic growth conditions, substrate for the MEP pathway in cyanobacteria may not derive from pyruvate and G3P. Rather, substrates originating from the pentose phosphate cycle may enter the pathway at steps later than MEP (Ershov et al, *J Bacteriol* 184: 5045-5051, 2002; Poliquin et al. 2004, supra) (FIG. 1), providing a more direct link between products photosynthesis and the isoprenoid biosynthetic pathway. Furthermore, it has been shown that, in the cyanobacterium *Thermosynechococcus elongatus* BP-1, the reaction catalyzed by GcpE, an Fe—S containing enzyme responsible for the formation of HMBPP, is dependent upon reduction by ferredoxin for its activity (Okada and Hase, *J Biol Chem* 280: 20672-20679, 2005) (FIG. 1), providing yet another direct link between photosynthesis and the isoprenoid biosynthesis pathway.

This invention in based, in part, on the discovery of nucleic acids and expression systems that provide production of short-chain hydrocarbons using genetically engineered cyanobacteria, e.g., *Synechocystis* sp. PCC6803, to generate improved new strains capable of isoprene ($C_5H_8$) production. Such genetically modified cyanobacteria can be used commercially in an enclosed mass culture system, e.g., (photo) bioreactors, to provide a source of renewable fuel for internal combustion engines or, upon on-board reformation, in fuel-cell operated engines; or to provide a source of isoprene for use in other chemical processes such as chemical synthesis.

BRIEF SUMMARY OF THE INVENTION

The invention is based, in part, on the discovery of improvements to the engineering of cyanobacteria which, upon suitable modification, produce 5-carbon isoprenoids. In one aspect, the invention therefore provides methods and compositions for producing and harvesting isoprene from cyanobacteria. Such genetically modified organisms can be used commercially in an enclosed mass culture system, e.g., to provide a source of renewable fuel for internal combustion engines or, upon on-board reformation, in fuel-cell operated engines; or to provide a source of isoprene for uses in other chemical processes such as chemical synthesis.

Cyanobacteria do not possess an isoprene synthase, which catalyzes the last committed step in isoprene ($C_5H_8$) formation. This invention therefore provides methods and compositions to genetically modify microorganisms to express an isoprene synthase gene, e.g., a codon-adjusted kudzu isoprene synthase gene, in order to produce isoprene ($C_5H_8$) in cyanobacteria.

In one aspect, the invention provides a method of producing isoprene hydrocarbons in cyanobacteria, the method comprising: introducing an expression cassette that comprises a nucleic acid encoding isoprene synthase into the cyanobacteria, wherein the nucleic acid encoding isoprene synthase is operatively linked to a PsbA2 promoter, or other suitable promoter; and culturing the cyanobacteria under conditions in which the nucleic acid encoding isoprene synthase is expressed. In some embodiments, the expression cassette is introduced into the PsbA2 gene locus and the PsbA2 promoter is the native cyanobacteria promoter. In some embodiments, the cyanobacteria are unicellular cyanobacteria, e.g., a *Synechocystis* sp or a *Synechococcus* sp. In alternative embodiments, the cyanobacteria are multicellular, e.g., a *Gloeocapsa* sp. The mutlicellular cyanobacteria may be a filamentous cyanobacteria sp. such as a *Nostoc* sp, an *Anabaena* sp, or an *Arthrospira* sp. In some embodiments, the nucleic acid encodes an isoprene synthase that has at least 55%, 60%, 70%, 75%, or 80% sequence identity, often at least 85%, 90%, or 95% sequence identity, to SEQ ID NO:2. In some embodiments, the nucleic acid encodes an isoprene synthase that comprises amino acid SEQ ID NO:2. Preferably, the nucleic acid that encodes the IspS is codon-adjusted for expression in cyanobacteria, e.g., in some embodiments, the nucleic acid is a codon-adjusted variant of SEQ ID NO:1 where codons used with an average frequency of less than 12% by *Synechocystis* are replaced by more frequently used codons. In some embodiments, the isoprene synthase nucleic acid comprises SEQ ID NO:3, or a sequence having at least 80% identity, typically at least 85% identity or 90% 95%, 96%, 97%, 98%, or 99% identity to SEQ ID NO:3.

In other aspects, the invention provides a cyanobacteria cell, wherein the cyanobacteria cell comprises a heterologous nucleic acid that encodes isoprene synthase and is operably linked to a PsbA2 promoter. In some embodiments, the cyanobacteria are unicellular cyanobacteria, e.g., a *Synechocystis* sp or a *Synechococcus* sp. In alternative embodiments, the cyanobacteria are multicellular cyanobacteria, e.g., a *Gloeocapsa* sp. In some embodiments, the multicellular cyanobacteria sp is a filamentous cyanobacteria sp. such as a *Nostoc* sp, an *Anabaena* sp, or an *Arthrospira* sp. In some embodiments, the heterologous nucleic acid encodes an isoprene synthase that has at least 55%, 60%, 70%, 75%, or 80% sequence identity, often at least 85%, 90%, or 95% sequence identity, to SEQ ID NO:2. In some embodiments, the cyanobacteria cell comprises a heterologous nucleic acid that encodes an isoprene synthase that comprises amino acid SEQ ID NO:2. Preferably, the heterologous nucleic acid introduced into the cyanobacterial cell that encodes the IspS is codon-adjusted for expression in cyanobacteria, e.g., in some embodiments, the nucleic acid is a codon-adjusted variant of SEQ ID NO:1 where codons used with an average frequency of less than 12% by *Synechocystis* are replaced by more frequently used codons. In some embodiments, the isoprene synthase nucleic acid comprises SEQ ID NO:3, or a sequence having at least 80%, 85%, 90%, 95%, 96%, 97%, 98%, or 99% identity to SEQ ID NO:3.

In another aspect, the invention provides a method of producing isoprene hydrocarbons in cyanobacteria as described herein that express an isoprene synthase gene, where the method comprises mass-culturing cyanobacteria as described above under conditions in which the isoprene synthase gene is expressed, e.g., high light conditions, (e.g., 500-2000 µmol photons $m^{-2} s^{-1}$) and harvesting the volatile isoprene produced by the cyanobacteria.

In a further aspect, the invention provides a nucleic acid encoding an isoprene synthase that comprises amino acid SEQ ID NO:2, where the nucleic acid is a codon-adjusted variant of SEQ ID NO:1 where codons used with an average frequency of less than 12% by *Synechocystis* are replaced by more frequently used codons. In some embodiments, the nucleic acid comprises the sequence set forth in SEQ ID NO:3, or a sequence having at least 80%, 85%, 90%, 95%, 96%, 97%, 98%, or 99% identity to SEQ ID NO:3. The invention additionally provides vectors comprising the nucleic acid and cyanobacterial host cells into which the nucleic acid has been introduced.

BRIEF DESCRIPTION OF THE DRAWINGS

FIG. 7. Western blot analysis showing expression of the kIspS protein in transformed strains of *Synechocystis*. (a) Top panel: Western blot analysis, with kIspS-specific polyclonal antibodies. Lane 1: wt *Synechocystis*; lanes 2-4: three different lines of kIspS-expressing *Synechocystis* transformants; lanes 5-7: three different lines of SkIspS-expressing *Synechocystis* transformants. Lower panel: Coomassie-stained SDS-PAGE profile of proteins corresponding to the Western blot above, shown as a control of equal protein loading. 20 μg protein were loaded in each lane. (b) Western blot analysis showing induction of expression of SkIspS in response to high-light treatment of *Synechocystis*. Top panel: Western blot analysis with kIspS specific polyclonal antibodies. Lane 1: wt *Synechocystis*; lanes 0.5-6 h, SkIspS-expressing *Synechocystis* transformant: samples taken at t=0 to t=6 h after a shift of the culture from low (10 μmol photons m−2 s−1) to high (500 μmol photons m−2 s−1) light. Middle panel: the same samples as in the top panel, probed with polyclonal antibodies directed against the AtpA protein, used as a control to show stable expression independent of the change in the light regime. Lower panel: Coomassie-stained SDS-PAGE profile of proteins corresponding to the Western blots above, shown as a control of equal protein loading. 20 μg protein were loaded in each lane.

FIG. 9. Alignment of IspS protein sequences (SEQ ID NOS:17-20).

DETAILED DESCRIPTION OF THE INVENTION

Definitions

Figure 1:
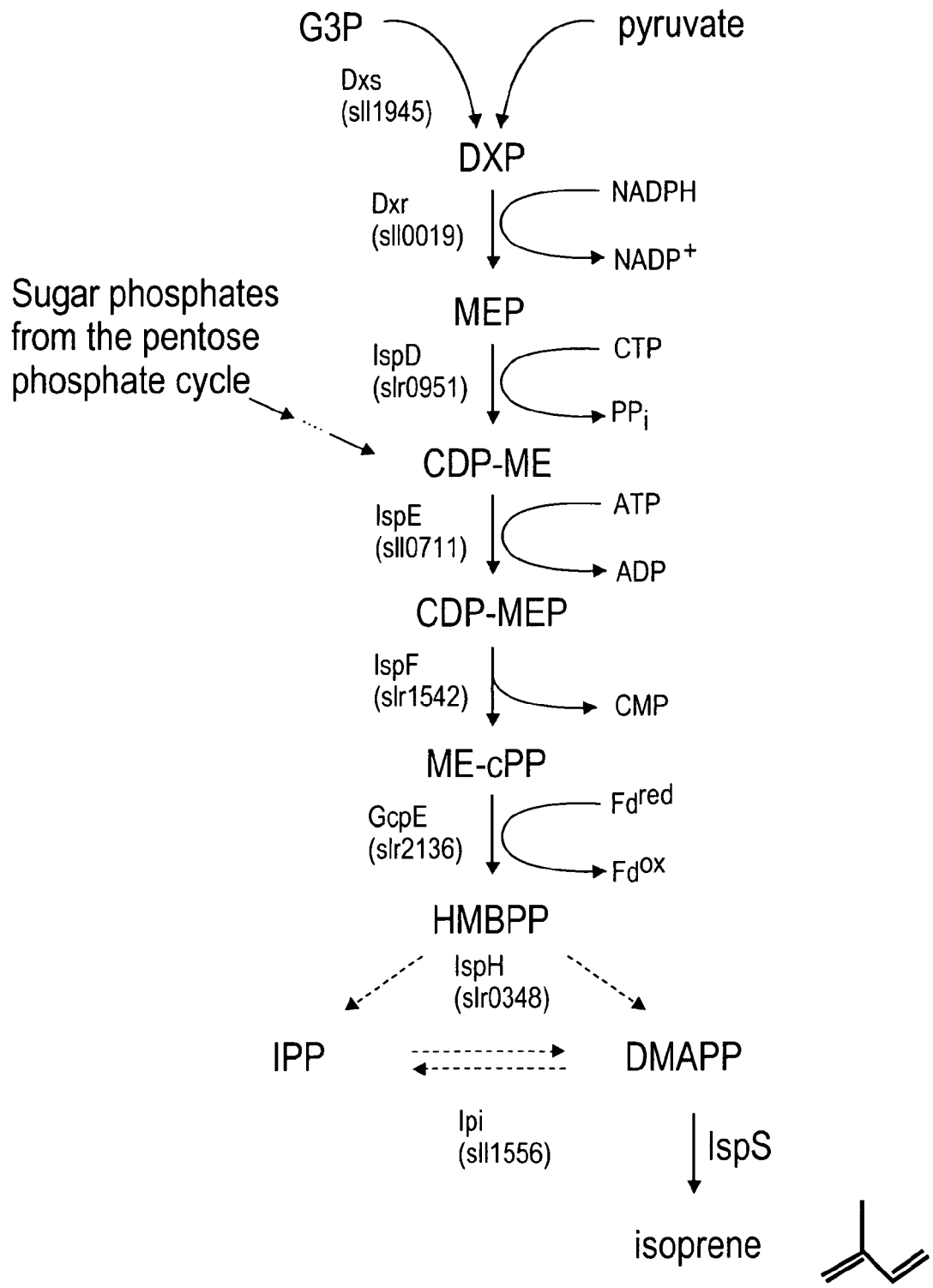
FIG. 1. MEP pathway for isoprene biosynthesis. Compounds: G3P=glyceraldehyde 3-phosphate; DXP=deoxyxylulose 5-phosphate; MEP=methylerythritol 4-phosphate; CDP-ME=diphosphocytidylyl methylerythritol; CDP-MEP=CDP-ME 2-phosphate; ME-cPP=methylerythritol 2,4-cyclodiphosphate; HMBPP=hydroxymethylbutenyl diphosphate; IPP=isopentenyl diphosphate; DMAPP=dimethylallyl diphosphate. Enzymes: Dxs=DXP synthase; Dxr=DXP reductoisomerase; IspD=CDP-ME synthase; IspE=CDP-ME kinase; IspF=ME-cPP synthase; GcpE (IspG) HMBPP synthase; Fd=ferredoxin; IspH=HMBPP reductase; Ipi=IPP isomerase; IspS=isoprene synthase. The corresponding ORF names in the *Synechocystis* genome database (http://genome.kazusa.or.jp/cyanobase/ (Kaneko and Tabata, *Plant Cell Physiol* 38: 1171-117, 1997)) are given in parentheses, where applicable. The pathway consumes reducing equivalents and energy in the form of NADPH, reduced ferredoxin, CTP and ATP, ultimately derived from photosynthesis. (See also Ershov et al., *J Bacteriol* 184: 5045-5051, 2002; Sharkey et al. 2008, supra).

A "volatile isoprene hydrocarbon" in the context of this invention refers to a 5-carbon, short chain isoprenoid, e.g., isoprene.

The terms "nucleic acid" and "polynucleotide" are used synonymously and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones. Thus, nucleic acids or polynucleotides may also include modified nucleotides, that permit correct read through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc The phrase "a nucleic acid sequence encoding" refers to a nucleic acid which contains sequence information for a structural RNA, or the primary amino acid sequence of a specific protein or peptide, or a binding site for a trans-acting regulatory agent. This phrase specifically encompasses degenerate codons (i.e., different codons which encode a single amino acid) of the native sequence or sequences that may be introduced to conform with codon preference in a specific host cell. In the context of this invention, the term "IspS coding region" when used with reference to a nucleic acid reference sequence such as SEQ ID NO:1 or 3 refers to the region of the nucleic acid that encodes IspS protein.

An IspS "gene" in the context of this invention refers to a nucleic acid that encodes an IspS protein, or fragment thereof. Thus, such a gene is often a cDNA sequence that encodes IspS. In other embodiments, an IspS gene may include sequences, such as introns, that are not present in a cDNA.

The term "promoter" or "regulatory element" refers to a region or sequence determinants located upstream or downstream from the start of transcription that direct transcription. As used herein, a promoter includes necessary nucleic acid sequences near the start site of transcription, such as, in the case of a polymerase II type promoter, a TATA element. A promoter also optionally includes distal elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter) and a second nucleic acid sequence, such as an IspS gene, wherein the expression control sequence directs transcription of the nucleic acid corresponding to the second sequence. A "cyanobacteria promoter" is a promoter capable of initiating transcription in cyanobacterial cells, respectively. Such a promoter is therefore active in a cyanobacteria cell, but need not originate from that organism. It is understood that limited modifications can be made without destroying the biological function of a regulatory element and that such limited modifications can result in cyanobacteria regulatory elements that have substantially equivalent or enhanced function as compared to a wild type cyanobacteria regulatory element. These modifications can be deliberate, as through site-directed mutagenesis, or can be accidental such as through mutation in hosts harboring the regulatory cyanobacteria regulatory element as long as the ability to confer expression in unicellular and multicellular cyanobacteria is substantially retained.

A "PsbA2 promoter" refers to a promoter region that regulates expression of psbA2. The promoter region the psbA2 gene has been well characterized (Eriksson et al., *Mol Cell*

*Biol Res Commun* 3: 292-298, 2000; Mohamed et al., *Mol Gen Genet*. 238: 161-168, 1993; Mohamed and Jansson, *Plant Mol Biol* 13: 693-700, 1989). Often, the PsbA2 promoter that is operably linked to an IspS gene of this invention is the endogenous cyanobacteria promoter, but a heterologous PsbA2 promoter may also be employed. Such promoter sequences typically include High Light Regulatory 1 (HLR1) sequences that are involved in photoregulation as well as minimal promoter sequences (see, e.g., Eriksson et al, supra, 2000).

"Expression" of an IspS gene in the context of this invention typically refers introducing an IspS gene into cyanobacteria cells, in which it is not normally expressed. Accordingly, an "increase" in IspS activity or expression is generally determined relative to wild type cyanobacteria that have no IspS activity.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants An "IspS polynucleotide" as used herein refers to a nucleic acid sequence that encodes SEQ ID NO:2, or to the IspS coding region of SEQ ID NO:1 or to SEQ ID NO:3; or a nucleic acid sequence that is substantially similar to the IspS coding region of SEQ ID NO:1 or to SEQ ID NO:3; or a nucleic acid sequence that encodes a polypeptide of SEQ ID NO:2, or a polypeptide that is substantially similar to SEQ ID NO:2, or a fragment or domain thereof. Thus, an IspS polynucleotide: 1) comprises a region of about 15 to about 50, 100, 150, 200, 300, 500, 1,000, 1500, or 1700 or more nucleotides, sometimes from about 20, or about 50, to about 1800 nucleotides and sometimes from about 200 to about 600 or about 1700 nucleotides of SEQ ID NO:1 or SEQ ID NO:3; or 2) hybridizes to SEQ ID NO:1 or SEQ ID NO:3, or the complements thereof, under stringent conditions, or 3) encodes an IspS polypeptide or fragment of at least 50 contiguous amino acids, typically of at least 100, 150, 200, 250, 300, 350, 400, 450, 500, or 550, or more contiguous residues of an IspS polypeptide, e.g., SEQ ID NO:2; or 4) encodes an IspS polypeptide or fragment that has at least 55%, often at least 60%, 65%, 70%, 75%, 80%, 85%, 90%, 95%, or greater identity to SEQ ID NO:2, or over a comparison window of at least 100, 200, 300, 400, 500, or 550 amino acid residues of SEQ ID NO:2; or 5) has a nucleic acid sequence that has greater than about 60%, 65%, 70%, 75%, 80%, 85%, 90%, 95%, 96%, 97%, 98%, 99%, or higher nucleotide sequence identity to SEQ ID NO:1 or SEQ ID NO:3, at least 80%, 85%, 90%, or at least 95%, 96%, 97%, 98%, 99% or greater identity over a comparison window of at least about 50, 100, 200, 500, 1000, 1500, 2000, or more nucleotides of SEQ ID NO:1 or SEQ ID NO:3; or 6) is amplified by primers to SEQ ID NO:1 or SEQ ID NO:3. The term "IspS polynucleotide" refers to double stranded or singled stranded nucleic acids. The IspS nucleic acids for use in the invention encode an active IspS that catalyzes the conversion of a dimethylallyl diphosphate substrate to isoprene.

A "codon-adjusted variant of an IspS nucleic acid", e.g., a codon-adjusted variant of SEQ ID NO:1, in the context of this invention refers to a variant that encodes the same protein, e.g., SEQ ID NO:2, but contains nucleotide substitutions based on frequency of codon occurrence in cyanobacteria.

An "IspS polypeptide" is an amino acid sequence that has the amino acid sequence of SEQ ID NO:2, or is substantially similar to SEQ ID NO:2, or a fragment or domain thereof. Thus, an IspS polypeptide can: 1) have at least 55% identity, typically at least 60%, 65%, 70%, 75%, 80%, 85%, 90%, 95% or greater identity to SEQ ID NO:2, or over a comparison window of at least 100, 200, 250, 300, 250, 400, 450, 500, or 550 amino acids of SEQ ID NO:2; or 2) comprise at least 100, typically at least 200, 250, 300, 350, 400, 450, 500, 550, or more contiguous amino acids of SEQ ID NO:2; or 3) bind to antibodies raised against an immunogen comprising an amino acid sequence of SEQ ID NO:2. An IspS polypeptide in the context of this invention is a functional protein that catalyzes the conversion of a dimethylallyl diphosphate substrate to isoprene.

As used herein, a homolog or ortholog of a particular IspS gene (e.g., SEQ ID NO:1) is a second gene in the same plant type or in a different plant type that is substantially identical (determined as described below) to a sequence in the first gene.

In the case of expression of transgenes one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "IspS polynucleotide sequence" or "IspS gene".

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. *APL. Math.* 2:482 (1981), by the homology alignment algorithm of Needle man and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. A "comparison window", as used herein, includes reference to a segment of any one of the number of contiguous positions, e.g., 20 to 600, usually about 50 to about 200, more usually about 100 to about 150 in which a sequence may be compared to a reference sequence of the same number of contiguous positions after the two sequences are optimally aligned.

The term "substantial identity" in the context of polynucleotide or amino acid sequences means that a polynucleotide or polypeptide comprises a sequence that has at least 50% sequence identity to a reference sequence. Alternatively, percent identity can be any integer from 50% to 100%. Exemplary embodiments include at least: 55%, 57%, 60%, 65%, 70%, 75%, 80%, 85%, 90%, 95%, or 99% identity compared to a reference sequence using the programs described herein; preferably BLAST using standard default parameters, as described below. Accordingly, IspS sequences of the invention include nucleic acid sequences that have substantial identity to the IspS coding region of SEQ ID NO:1 or to SEQ ID NO:3. As noted above, IspS polypeptide sequences of the invention include polypeptide sequences having substantial identify to SEQ ID NO:2.

Polypeptides that are "substantially similar" share sequences as noted above except that residue positions that are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 55° C., 60° C., or 65° C. Such washes can be performed for 5, 15, 30, 60, 120, or more minutes.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. For example, an IspS polynucleotides, can also be identified by their ability to hybridize under stringency conditions (e.g., Tm ~40° C.) to nucleic acid probes having the sequence of SEQ ID NO:3. Such an IspS nucleic acid sequence can have, e.g., about 25-30% base pair mismatches or less relative to the selected nucleic acid probe. SEQ ID NO:3 is an exemplary IspS polynucleotide sequence. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

The term "isolated", when applied to a nucleic acid or protein, denotes that the nucleic acid or protein is essentially free of other cellular components with which it is associated in the natural state. It is preferably in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest.

As used herein, "mass-culturing" refers to growing large quantities of cyanobacteria, that have been modified to express an IspS gene. A "large quantity" is generally in the range of about 100 liters to about 1,500,000 liters, or more. In some embodiments, the organisms are cultured in large quantities in modular bioreactors, each having a capacity of about 1,000 to about 1,000,000 liters.

A "bioreactor" in the context of this invention is any enclosed large-capacity vessel in which cyanobacteria are grown. A "large-capacity vessel" in the context of this invention can hold about 100 liters, often about 500 liters, or about 1,000 liters to about 1,000,000 liters, or more.

As used herein, "harvesting" volatile isoprene hydrocarbons refers to capturing and sequestering such hydrocarbons in a closed or contained environment.

IspS Nucleic Acid Sequences

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel et al., eds., 1994-1999).

IspS nucleic acid and polypeptide sequences are known in the art. IspS genes have been isolated and sequenced from poplar and aspen (two related trees), and kudzu (a vine). The species involved and the sequences available in the NCBI database are given below by accession number, each of which is incorporated by reference:

*Populus alba* (white poplar) IspS mRNA for isoprene synthase; ACCESSION No AB198180;

*Populus tremuloides* (quaking aspen) isoprene synthase (IspS); ACCESSION No AY341431 (complete cds);

*Populus alba×Populus tremula* IspS mRNA; ACCESSION No AJ294819;

*Populus nigra* (Lombardy poplar) mRNA for isoprene synthase (IspS gene); ACCESSION No AM410988;

*Pueraria montana* var. *lobata* (kudzu vine) isoprene synthase (IspS); ACCESSION No AY316691 (complete cds.).

Examination of these IspS sequences reveals a high degree of nucleotide and amino acid sequence identities, for example, hybrid poplar and aspen cDNA sequences are 98% identical at the polypeptide and nucleotide level (see, e.g., Sharkey et al., *Plant Physiol.* 137:700-712, 1995). The aspen isoprene synthase nucleotide coding sequence is 65% identical to the kudzu gene, while the protein sequences (without the chloroplast transit peptide) are 57% identical.

Figure 9:
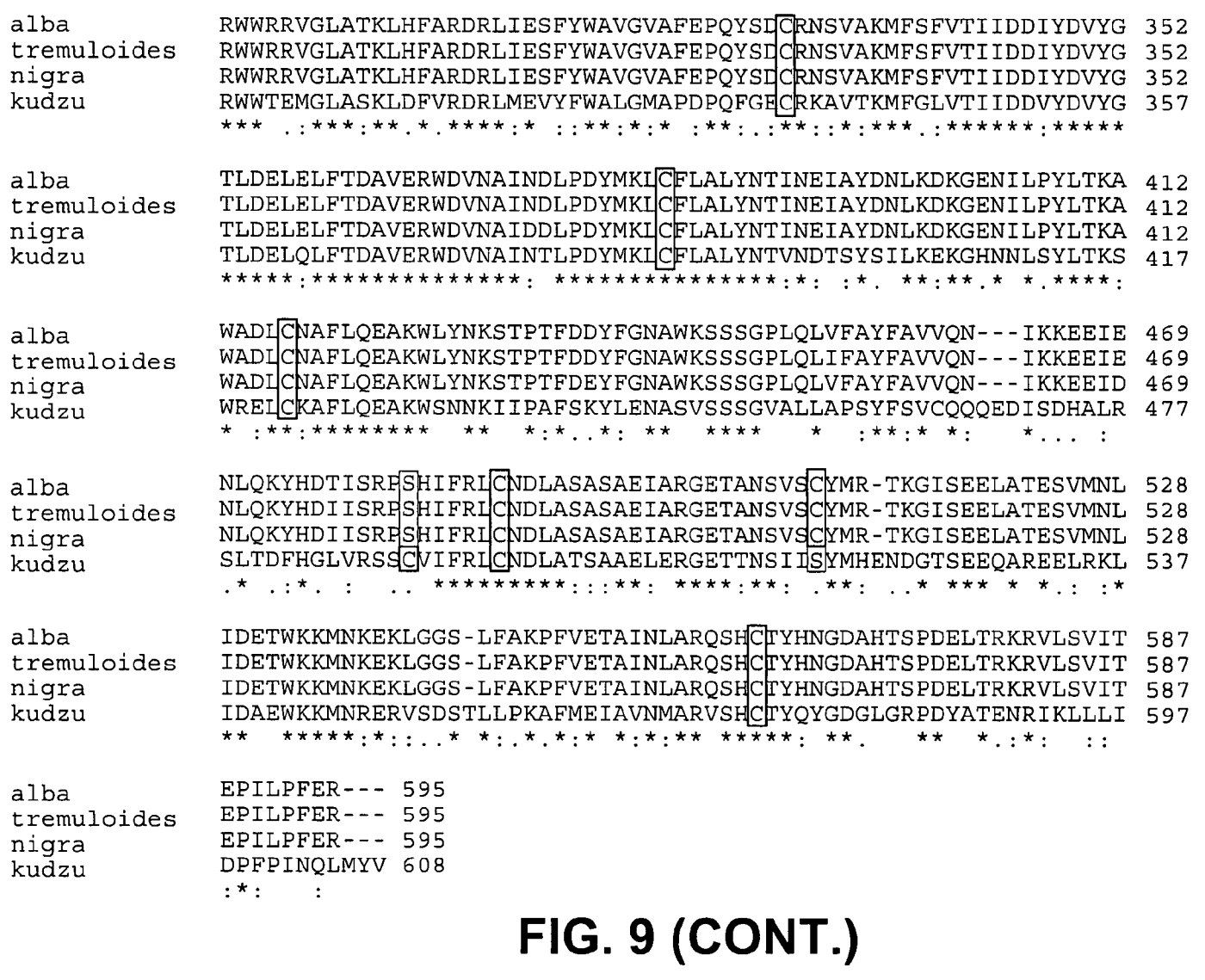

The poplar IspS protein has a high-density of Cysteine and Histidine amino acids in the carboxy-terminal half of the protein. For example, considering the 591 amino acid sequence of the Cr-IspS protein, cysteine moieties are found at positions 34, 326, 378, 413, 484, 505 and 559, i.e., six out of the seven cysteines are found in the lower 45% of the protein. Additional clustering of histidines in various positions of the C-terminal half of the protein is also observed. Cysteine and histidine amino acids are known to participate in proper folding and catalytic site structure of proteins and can be important components for enzyme activity. An alignment of four known IspS proteins showing the high conservation of Cys in the C-terminal part of the molecule is provided in FIG. 9. In one case, the kudzu protein has substituted an otherwise conserved Cys with Ser (Cys-509-Ser of the Alba or nigra or tremuloides) sequence in the clustal alignment in FIG. 9). Serine is a highly conservative substitution for cysteine, as the only difference between the two amino acids is a —OH group in the place of the —SH group. In fact, examination of the four IspS sequences reveals the additional property of many conserved Serines in the C-terminal half of the protein. Accordingly, in some embodiments, a nucleic acid for use in the invention encodes an IspS polypeptide that comprises the carboxyl-terminal 45% of SEQ ID NO:2 and retain the catalytic activity in converting DMAPP to isoprene. Other examples exist where a related protein in one microorganism, such as a green microalgae, lacks a substantial portion of the N-terminal portion of the protein (relative to the form of the protein present in another microorganism such as bacteria) without adverse effect on activity (see, e.g., Melis and Happe, *Plant Physiol.* 127:740-748, 2001). Accordingly, in some embodiments, an IspS nucleic acid for use in the invention encodes a polypeptide that comprises from about amino acid residue 300 through the C-terminus of SEQ ID NO:2. In some embodiments, the IspS polypeptide encoded by the IspS nucleic acid comprises from about amino acid residue 300 through the C-terminus of SEQ ID NO:2. In some embodiments, the IspS sequence can additionally lack the last 10, 15, or 20 residues of SEQ ID NO:2.

The transit peptide of the IspS protein includes, minimally, amino acids 1-37 for poplar and aspen and 1-39 for kudzu (not including a methionine encoded by the start ATG). IspS nucleic acid sequences for use in the invention typically do not include sequences that encode a transit polypeptide and further may omit additional N-terminal sequence.

In some embodiments of the invention, a nucleic acid sequence that encodes a poplar or aspen IspS polypeptide may be used. In typical embodiments, a nucleic acid sequence that encodes a kudzu IspS polypeptide (e.g., SEQ ID NO:2) is used. The IspS polypeptides encoded by the nucleic acids employed in the methods of the invention have the catalytic activity of converting DMAPP to isoprene. Typically, the level of activity is equivalent to the activity exhibited by a natural kudzu IspS polypeptide (e.g., encoded by SEQ ID NO:1).

Isolation or generation of IspS polynucleotide sequences can be accomplished by well known techniques, including amplification techniques and/or library screening.

Appropriate primers and probes for generating an IspS gene can be designed based on known principles using, e.g., the IspS sequences provided herein. For a general overview of PCR see PCR Protocols: A Guide to Methods and Applications. (Innis, M, Gelfand, D., Sninsky, J. and White, T., eds.), Academic Press, San Diego (1990). An exemplary PCR for amplifying an IspS nucleic acid sequence is provided in the examples.

The genus of IspS nucleic acid sequences for use in the invention includes genes and gene products identified and characterized by techniques such as hybridization and/or sequence analysis using exemplary nucleic acid sequences, e.g., SEQ ID NO:1 or SEQ ID NO:3.

Preparation of Recombinant Vectors

To use isolated sequences in the above techniques, recombinant DNA vectors suitable for transformation of cyanobacteria are prepared. Techniques for transformation are well known and described in the technical and scientific literature. For example, a DNA sequence encoding an IspS gene (described in further detail below), can be combined with transcriptional and other regulatory sequences which will direct the transcription of the sequence from the gene in the intended cells of the transformed cyanobacteria. In some embodiments, an expression vector that comprises an expression cassette that comprises the IspS gene further comprises a promoter operably linked to the IspS gene. In other embodiments, a promoter and/or other regulatory elements that direct transcription of the IspS gene are endogenous to the microorganism and the expression cassette comprising the IspS gene is introduced, e.g., by homologous recombination, such that the heterologous IspS gene is operably linked to an endogenous promoter and is expression driven by the endogenous promoter.

Regulatory sequences include promoters, which may be either constitutive or inducible. In some embodiments, a promoter can be used to direct expression of IspS nucleic acids under the influence of changing environmental conditions. Examples of environmental conditions that may effect transcription by inducible promoters include anaerobic conditions, elevated temperature, or the presence of light. Promoters that are inducible upon exposure to chemicals reagents are also used to express IspS nucleic acids. Other useful inducible regulatory elements include copper-inducible regulatory elements (Mett et al., *Proc. Natl. Acad. Sci. USA* 90:4567-4571 (1993); Furst et al., *Cell* 55:705-717 (1988)); tetracycline and chlor-tetracycline-inducible regulatory elements (Gatz et al., *Plant J.* 2:397-404 (1992); Röder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible promoters, such as those of the hsp70/dnaK genes (Takahashi et al., *Plant Physiol.* 99:383-390 (1992); Yabe et al., *Plant Cell Physiol.* 35:1207-1219 (1994); Ueda et al., *Mol. Gen. Genet.* 250:533-539 (1996)); and lac operon elements, which are used in combination with a constitutively expressed lac repressor to confer, for example, IPTG-inducible expression (Wilde et al., EMBO J. 11:1251-1259 (1992)). An inducible regulatory element also can be, for example, a nitrate-inducible promoter, e.g., derived from the spinach nitrite reductase gene (Back et al., *Plant Mol. Biol.* 17:9 (1991)), or a light-inducible promoter, such as that associated with the small subunit of RuBP carboxylase or the LHCP gene families (Feinbaum et al., *Mol. Gen. Genet.* 226:449 (1991); Lam and Chua, Science 248:471 (1990)), or a light.

In some embodiments, the promoter may be from a gene associated with photosynthesis in the species to be transformed or another species. For example such a promoter from one species may be used to direct expression of a protein in transformed cyanobacteria cells. Suitable promoters may be isolated from or synthesized based on known sequences from other photosynthetic organisms. Preferred promoters are those for genes from other photosynthetic species, or other photosynthetic organism where the promoter is active in cyanobacteria.

In some embodiments, a promoter used to drive expression of a heterologous IspS gene is a constitutive promoter. Examples of constitutive strong promoters for use in cyanobacteria include, for example, the psbDI gene or the basal promoter of the psbDII gene. Various other promoters that are active in cyanobacteria are also known. These include the light inducible promoters of the psbA and psbA3 genes in cyanobacteria and promoters such as those set forth in U.S. Patent Application Publication No. 20020164706, which is incorporated by reference. Other promoters that are operative in plants, e.g., promoters derived from plant viruses, such as the CaMV35S promoters, can also be employed in cyanobacteria. For a description of strong and regulated promoters, e.g., active in the cyanobacterium *Anabaena* sp. strain PCC 7120, see e.g., Elhai, *FEMS Microbiol Lett* 114:179-184, 1993).

In some embodiments, promoters are identified by analyzing the 5' sequences of a genomic clone corresponding to an IspS gene. Sequences characteristic of promoter sequences can be used to identify the promoter.

A promoter can be evaluated, e.g., by testing the ability of the promoter to drive expression in cyanobacteria in which it is desirable to introduce an IspS expression construct.

A vector comprising IspS nucleic acid sequences will typically comprise a marker gene that confers a selectable phenotype on cyanobacteria transformed with the vector. Such markers are known. For example, the marker may encode antibiotic resistance, such as resistance to kanamycin, G418, bleomycin, hygromycin, and the like.

IspS nucleic acid sequences of the invention are expressed recombinantly in cyanobacteria. Expression constructs can be designed taking into account such properties as codon usage frequencies of the organism in which the IspS nucleic acid is to be expressed. Codon usage frequencies can be tabulated using known methods (see, e.g., Nakamura et al. *Nucl. Acids Res.* 28:292, 2000). Codon usage frequency tables, including those for cyanobacteria, are also available in the art (e.g., in codon usage databases of the Department of Plant Genome Research, Kazusa DNA Research Institute available on the world side web kazusa.or.jp/codon.)

In some embodiments, the invention provides an IspS gene that encodes a kudzu IspS protein, where the gene is a codon-adjusted variant of a kudzu IspS gene, e.g., a codon-adjusted variant of SEQ ID NO:1. In preferred embodiments, codons of SEQ ID NO:1 that would be used at an average frequency of less than 12% by the cyanobacteria of interest are replaced by codons more frequently used.

Cell transformation methods and selectable markers for cyanobacteria are well known in the art (Wirth, *Mol Gen Genet.* 1989 March; 216(1):175-7; Koksharova, *Appl Microbiol Biotechnol* 2002 February; 58(2): 123-37; Thelwell). Transformation methods and selectable markers for are also well known (see, e.g., Sambrook et al., supra).

Microorganisms that can be Targeted

IspS can be expressed in any number of cyanobacteria where it is desirable to produce isoprene. Suitable unicellular cyanobacteria include *Synechocystis* sp., such as strain *Synechocystis* PCC 6803; and *Synechococcus* sp., e.g., the thermophilic *Synechococcus lividus*; the mesophilic *Synechococcus elongatus* or *Synechococcus* 6301. Multicellular, including filamentous cyanobacteria, may also be engineered to express IspS in accordance with this invention. Multicelulalr cyanobacteris that can be used include, e.g., *Gloeocapsa*, as well as filamentous cyanobacteria such as *Nostoc* sp., e.g., *Nostoc* sp. PCC 7120, *Nostoc sphaeroides*); *Anabaena* sp., e.g., *Anabaena variabilis*; and *Arthrospira* sp. ("Spirulina"), such as *Arthrospira platensis* and *Arthrospira maxima*.

Transformed cyanobacteria that express a heterologous IspS gene are grown under mass culture conditions for the production of hydrocarbons, e.g., to be used as a fuel source or as feedstock in synthetic chemistry. The transformed organisms are growth in bioreactors or fermentors that provide an enclosed environment to contain the hydrocarbons. In typical embodiments for mass culture, the cyanobacteria are grown in enclosed reactors in quantities of at least about 500 liters, often of at least about 1000 liters or greater, and in some embodiments in quantities of about 1,000,000 liters or more. One of skill understands that large scale culture of transformed cyanobacteria that comprise an isoprene synthase gene where expression is driven by a light sensitive promoter such as a PsbA2 promoter is typically carried out in conditions where the culture is exposed to natural light. Accordingly, in such embodiments appropriate enclosed reactors are used that allow light to reach the cyanobacteria culture.

Conditions for growing IspS-expressing cyanobacteria for the exemplary purposes illustrated above are known in the art (see, e.g., the exemplary references cited herein). Volatile isoprene hydrocarbons produced by the modified cyanobacteria can be harvested using known techniques. Isoprene hydrocarbons are not miscible in water and they rise to and float at the surface of the microorganism growth medium. They are siphoned off from the surface and sequestered in suitable containers. In addition, and depending on the prevailing temperature during the mass cultivation of the cyanobacteria, isoprene can exist in vapor form above the water medium in the bioreactor container (isoprene boiling temperature T=34° C.). Isoprene vapor is piped off the bioreactor container and condensed into liquid fuel form upon cooling or low-level compression.

Culture of Cyanobacterial Organisms and Isoprene Synthase Expression

Cyanobacteria of the invention in which expression of IspS is driven by a PsbA2 promoter can be grown in a range of lighting conditions, e.g., in 100% sunlight, e.g., about 2,000 µmol photons $m^{-2}$ $s^{-1}$ under direct sunlight, or in reduced light intensity conditions. Thus, such cyanobacteria cultures are generally exposed to light conditions that range from about 50 µmol photons $m^{-2}$ $s^{-1}$ cultures to about 2,500 µmol photons $m^2$ $s^{-1}$. In typical embodiments of the invention, cyanobacteria cultures of the invention produce at least about 2 micrograms isoprene per liter of culture per hour under limiting illumination conditions, e.g., at a light intensity of approximately 100 µmol photons $m^{-2}$ $s^{-1}$ and more, for example at least about 40 micrograms or more, of isoprene per liter of culture per hour, e.g., under 100% sunlight. For purposes of the preceding examples of yields, the amounts per liter refer to cultures that are grown to a density of about OD730=~0.5, which approximates about 1.6 mg chlorophyll per liter culture, or about 0.12 g dry cell weight per liter culture.

In typical embodiments, cyanobacteria are transformed with an expression vector comprising an IspS gene and an antibiotic resistance gene. Transformants are cultured in selective media containing an antibiotic to which an untransformed host cell is sensitive. Cyanobacteria normally have up to 100 copies of circular DNA in each cell. Successful transformation with an expression vector comprising an IspS gene and an antibiotic resistance gene normally occurs in only one, or just a few, of the many cyanobacterial DNA copies. Hence, presence of the antibiotic is necessary to encourage expression of the transgenic copy(ies) of the DNA for isoprene production. In the absence of the selectable marker (antibiotic), the transgenic copy(ies) of the DNA would be lost and replaced by wild-type copies of the DNA.

In some embodiments, IspS cyanobacterial transformants are cultured in the laboratory under continuous selective pressure conditions (presence of antibiotic over many generations) to achieve DNA homoplasmy in the transformed host organism. One of skill in the art understands that the number of generations and length of time of culture varies depending on the particular culture conditions employed. Homoplasmy can be determined, e.g., by monitoring the culture to determine the presence of wild-type copies of the cyanobacterial DNA.

"Achieving homoplasmy" refers to a quantitative replacement of most, e.g., 70% or greater, or typically all, wild-type copies of the cyanobacterial DNA in the cell with the transformant DNA copy that carries the IspS transgene. This is normally attained over time, under the continuous selective pressure (antibiotic) conditions applied, and entails the gradual during growth replacement of the wild-type copies of the DNA with the transgenic copies, until no wild-type copy of the cyanobacterial DNA is left in any of the transformant cells. Achieving homoplasmy is typically verified by quantitative amplification methods such as genomic-DNA PCR using primers and/or probes specific for the wild type copy of the cyanobacterial DNA. In some embodiments, the presence of wildtype cyanobacterial DNA can be detected by using primers specific for the wildtype cyanobacterial DNA and detecting the presence of the PsbA2 gene. Transgenic DNA is typically stable under homoplasmy conditions and present in all copies of the cyanobacterial DNA.

In some embodiments, cyanobacterial cultures can be cultured under conditions in which the light intensity is varied. Thus, for example, when a psbA2 promoter is used as a promoter to drive isoprene synthase expression, transformed cyanobacterial cultures can be grown at low light intensity conditions (e.g., 10-50 μmol photons $m^{-2} s^{-1}$), then shifted to higher light intensity conditions (e.g., 500 μmol photons $m^{-2} s^{-1}$). The psbA2 promoter responds to the shift in light intensity by up-regulating the expression of the IspS gene in *Synechocystis*, typically at least about 10-fold. In other embodiments, cyanobacterial cultures can be exposed to increasing light intensity conditions (e.g., from 50 μmol photons $m^{-2} s^{-1}$ to 2,500 μmol photons $m^{-2} s^{-1}$) corresponding to a diurnal increase in light intensity up to full sunlight. The psbA2 promoter responds to the gradual increase in light intensity by up-regulating the expression of the IspS gene in *Synechocystis* in parallel with the increase in light intensity.

In some embodiments, IspS gene expression is measured by quantitative Western blot analysis, where the amount of the IspS protein present in the cell is quantified. In other embodiments, IspS gene expression is measured by the amount of isoprene product accumulated in the headspace of the culture as a function of time (rate and yield of isoprene production).

EXAMPLES

The examples described herein are provided by way of illustration only and not by way of limitation. Those of skill in the art will readily recognize a variety of non-critical parameters that could be changed or modified to yield essentially similar results.

Example 1

Design and Expression of a kIspS and a SkIspS Gene for Isoprene Hydrocarbon Production in Cyanobacteria Materials and Methods
Strains and Growth Conditions

*Escherichia coli* strain XL1-Blue (Stratagene, La Jolla, Calif., USA), was used for routine subcloning and plasmid propagation. *E. coli* strain Rosetta (Novagen (EMD), San Diego, Calif., USA), was used for overexpression of recombinant protein to serve as antigen for antibody generation. All *E. coli* strains were grown in LB media with addition of appropriate antibiotics at 37° C., according to standard protocols. Overexpression of recombinant proteins was performed at 15° C.

*Synechocystis* sp. PCC 6803 (hereafter referred to as "*Synechocystis*") was grown routinely in BG11 medium (Stanier et al. 1971) at 25° C., and at a light intensity of approximately 40 μmol photons m–2 s–1. For the growth of transformed strains, 5 μg/ml kanamycin (Invitrogen, Carlsbad, Calif., USA) was added to liquid BG11 medium. For maintenance of strains on agar plates, the BG11 medium was supplemented with 1.5% (w/v) agar, 0.3% (w/v) sodium thiosulfate, and buffered with 10 mM TES-NaOH at pH 8.0.

Chlorophyll Determination

For chlorophyll (Chl) measurements, pigments were extracted in 90% methanol, cell debris removed by centrifugation at 20,000 g for 5 min, and the absorbance of the supernatant was measured using a Shimadzu UV 160U spectrophotometer. Chl a concentrations were calculated according to Meeks and Castenholz (1971).

Codon Adjustment and Gene Synthesis

The nucleotide sequence of the *Pueraria montana* (kudzu) isoprene synthase (IspS) gene (hereafter referred to as kIspS) was adjusted to the preferred codon usage of *Synechocystis* using the GeneDesigner software (DNA 2.0, Menlo Park, Calif., USA) and a *Synechocystis* codon usage table from the Kazusa Codon Usage Database (Nakamura et al. 2000). The native kudzu (kIspS) and *Synechocystis* codon-adjusted kudzu IspS (SkIspS) genes were augmented by suitable restriction sites and synthesized for use in this work by DNA 2.0 (Menlo Park, Calif., USA).

Construction of Plasmids for Transformation of *Synechocystis* with the Isoprene Synthase Gene For heterologous expression of the isoprene synthase gene in *Synechocystis*, plasmid constructs were generated, which allowed replacement of the psbA2 gene of *Synechocystis* with either the kIspS or SkIspS genes via double homologous recombination. Two regions of the *Synechocystis* genomic DNA containing 500 bp of sequence located immediately upstream and downstream, respectively, of the psbA2-gene were amplified by PCR. The primers used were A2us_Eco_F, 5'-GAGAGAGAATTCAGCGTTCCAGTGGAT 3' (SEQ ID NO:4), and A2us_NdeI_Bam_R, 5' GTTGGATCCGTCGT-TGTCATATGGTTATAA 3' (SEQ ID NO:5), for amplification of the upstream region; and A2ds_Bam_F, 5' GAGAGAGAGGATCCTTGGTGTAATGCC 3' (SEQ ID NO:6), and A2ds_SacI_R, 5' GAGAGAGAGAGCTC-GATCGCCTTGGCAAAACAA 3' (SEQ ID NO:7), for amplification of the downstream region. The upstream fragment was cloned in the EcoRI and BamHI sites of pBluescript KS+ (Stratagene, La Jolla, Calif., USA). The downstream fragment was subsequently cloned in the BamHI and SacI sites of the resulting vector to form pBA2A2. Thereafter, the kIspS or SkIspS synthetic genes were introduced into the NdeI and BamHI restriction sites of pBA2A2, forming plasmids pBA2kIA2 and pBA2SkIA2, respectively. The NdeI site allowed cloning of the IspS genes in frame with the translation start site of the replaced psbA2. The final step in the generation of the plasmid constructs was cloning of an antibiotic resistance cassette carrying npt gene, which is conferring resistance to kanamycin, into the single BamHI site of pBA2kIA2 and pBA2SkIA2, to form pBA2kIKmA2 and pBA2SkIKmA2 (see figure below). These two vectors were used to transform *Synechocystis*, as described below.

Transformation of *Synechocystis*

*Synechocystis* cultures were grown in liquid BG11 medium for 2-3 days until the cell density reached about $3 \times 10^7$ cells/ml (OD730=0.3). Cells were harvested by centrifugation and resuspended in fresh BG11 to a density of $10^9$ cells/ml. One μg of plasmid DNA was added to 100 μl of cell suspension in a microcentrifuge tube and mixed. The mixture was incubated at 25° C. under low light for 4-6 hours before spreading on nitrocellulose filters (HAWG, Millipore, Billerica, Mass., USA), which were placed on top of BG11 agar plates. After incubation for 24 h on BG11 agar, the filters were moved to selective media on BG11 agar plates containing 5 μg/ml kanamycin. Single colonies were isolated after about two weeks incubation, and grown in liquid culture for analysis.

Generation of IspS Polyclonal Antibodies

The native kudzu isoprene synthase cDNA sequence (kIspS) ((Sharkey et al. 2005), GenBank accession no AY316691) was cloned in an expression vector carrying a His-tag, which was subsequently used to transform *E. coli* (Rosetta, Novagen (EMD), San Diego, Calif., USA). After expression, the recombinant protein was purified on a Superflow Ni-NTA agarose column (Qiagen, Valencia, Calif., USA) according to the manufacturer's instructions. The purified protein was used as antigen for the generation of specific polyclonal antibodies (Covance, Princeton, N.J., USA).

Reverse transcription (RT-) PCR

For RT-PCR experiments, total RNA was extracted from 10 ml of cell culture, using Trizol reagent (Invitrogen, Carlsbad, Calif., USA) according to the manufacturer's instructions. RT-PCR was performed using 0.25 μg of total RNA as starting material for cDNA generation by SuperScript II reverse transcriptase (Invitrogen, Carlsbad, Calif., USA), followed by amplification by PCR. The following gene-specific primers were used:
RT_kIspS_F, 5' TCTTGGCTTTGAGGGAGAAA 3' (SEQ ID NO:8), and
RT_kIspS_R, 5' CCACCACCTTGACAGGTCTT 3' (SEQ ID NO:9), for amplification of kIspS;
RT_SkIspS_F, 5' CGGTCCTTAACGGACTTTCA 3' (SEQ ID NO:10), and
RT_SkIspS_R, 5' ATCGCCGTATTGGTAAGTGC 3' (SEQ ID NO:11), for amplification of SkIspS;
RT_rbcL_F, 5' GTATCACCATGGGCTTCGTT 3' (SEQ ID NO:12), and
RT_rbcL_R, 5' CACAAGCTTCCAAAGCAACA 3' (SEQ ID NO:13), for amplification of rbcL, which was used as a positive control of transcription.

Southern Blot Analysis

Genomic DNA from *Synechocystis* strains was extracted as previously described (Tamagnini et al. 1997). For Southern blots, 1 μg of each DNA sample was digested with a combination of two restriction enzymes; XbaI and SacI, or XbaI and NdeI. The digested DNA samples were separated on agarose gel and blotted onto a nylon membrane (Amersham Hybond N+, GE Healthcare, Little Chalfont, UK) according to the manufacturer's instructions. Detection of DNA fragments was performed using the Amersham Gene Images AlkPhos Direct Labeling and Detection System (GE Healthcare, Little Chalfont, UK). The probe used for detection was generated by PCR, using primers:
A2us_probe_R, 5' GAGTTTTGTAAAGCTTTGTAA-CAGGA 3' (SEQ ID NO:14), and
A2us_Eco_F, 5'-GAGAGAGAATTCAGCGTTCCAGTG-GAT 3' (SEQ ID NO:15), with *Synechocystis* genomic DNA as template for the reaction, and labeled according to the manufacturer's instructions.

SDS-PAGE and Western Blot Analysis

For Western blot analysis, *Synechocystis* crude extracts were prepared by sonication of cells in Tris-EDTA-NaCl (TEN) buffer (50 mM Tris-HCl pH 8, 5 mM EDTA, 100 mM NaCl) with addition of a mix of protease inhibitors (P2714, Sigma-Aldrich, St Louis, Mo., USA). After sonication, insoluble material was removed by centrifugation, and the protein concentration of the supernatant determined using the Bio-Rad DC assay (Bio-Rad Laboratories, Hercules, Calif., USA). The soluble protein extracts were separated on 8-12% SDS-PAGE according to Laemmli (Laemmli 1970), blotted onto PVDF membranes (Millipore, Billerica, Mass., USA), according to standard procedure, and probed sequentially with primary specific polyclonal antibodies and horseradish peroxidase conjugated secondary antibodies (Bio-Rad Laboratories, Hercules, Calif., USA). Cross-reactions between protein bands and antibodies were visualized using the Supersignal ECL detection kit (Pierce, Thermo Fisher Scientific Inc., Rockford, Ill., USA) following the manufacturer's instructions. The antiserum against the AtpA protein was described previously (Park and Rodermel 2004).

IspS and Isoprene Production Activity Assays

To assay isoprene synthase activity, gas from the headspace of sealed cultures was sampled and analyzed by gas chromatography using a Shimadzu 8A GC (Shimadzu, Columbia, Md., USA) equipped with a flame ionization detector (FID) and a column selected to detect short-chain hydrocarbons. Amounts of isoprene produced were estimated by comparison with a pure isoprene standard (Acros Organics, Fair Lawn, N.J., USA)

Expression in *E. coli* and *Synechocystis*

Figure 2:
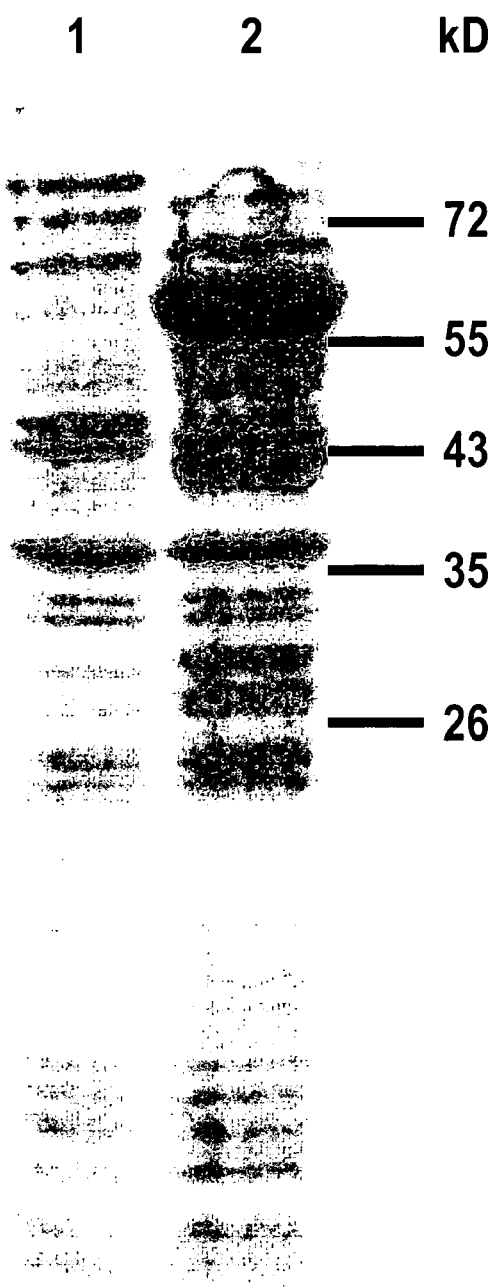
FIG. 2. SDS-PAGE profile of whole cell *E. coli* extract of proteins, isolated from un-induced (lane 1) and induced (lane 2) cells. The IspS protein in the induced cells (lane 2) is visible as a pronounced 65 kD polypeptide.

The isoprene synthase IspS gene from the vine *Pueraria montana* (kudzu) was used for expression of the enzyme in *E. coli* and *Synechocystis*. The native cDNA sequence was first employed (GenBank accession no AY316691) (Sharkey et al., 2005, supra). The nucleotide sequence encoding the 39 amino acid (not counting the methionine-encoded by the start ATG) chloroplast transit peptide (not including the start methionine) was removed, resulting in a cDNA sequence encoding the mature IspS sequence only. This modified kudzu native IspS gene was cloned in an expression vector also including a 6× His (SEQ ID NO:16) tag epitope. The tagged recombinant protein was expressed in *E. coli*, and could be resolved on Coomassie stained SDS-PAGE of whole-cell extracts. FIG. 2 shows such an SDS-PAGE analysis, where protein samples were prepared from whole-cell extracts of uninduced (lane 1; not expressing His-kIspS) and induced (lane 2; expressing the His-kIspS) *E. coli*. The overexpressed His-kIsps protein is shown as a dominant 65 kD band in the induced cell extract only (FIG. 2, lane 2). Using the His-tag epitope, the kIspS protein was purified and subsequently used for the generation of specific polyclonal antibodies against the isoprene synthase protein.

Figure 3:
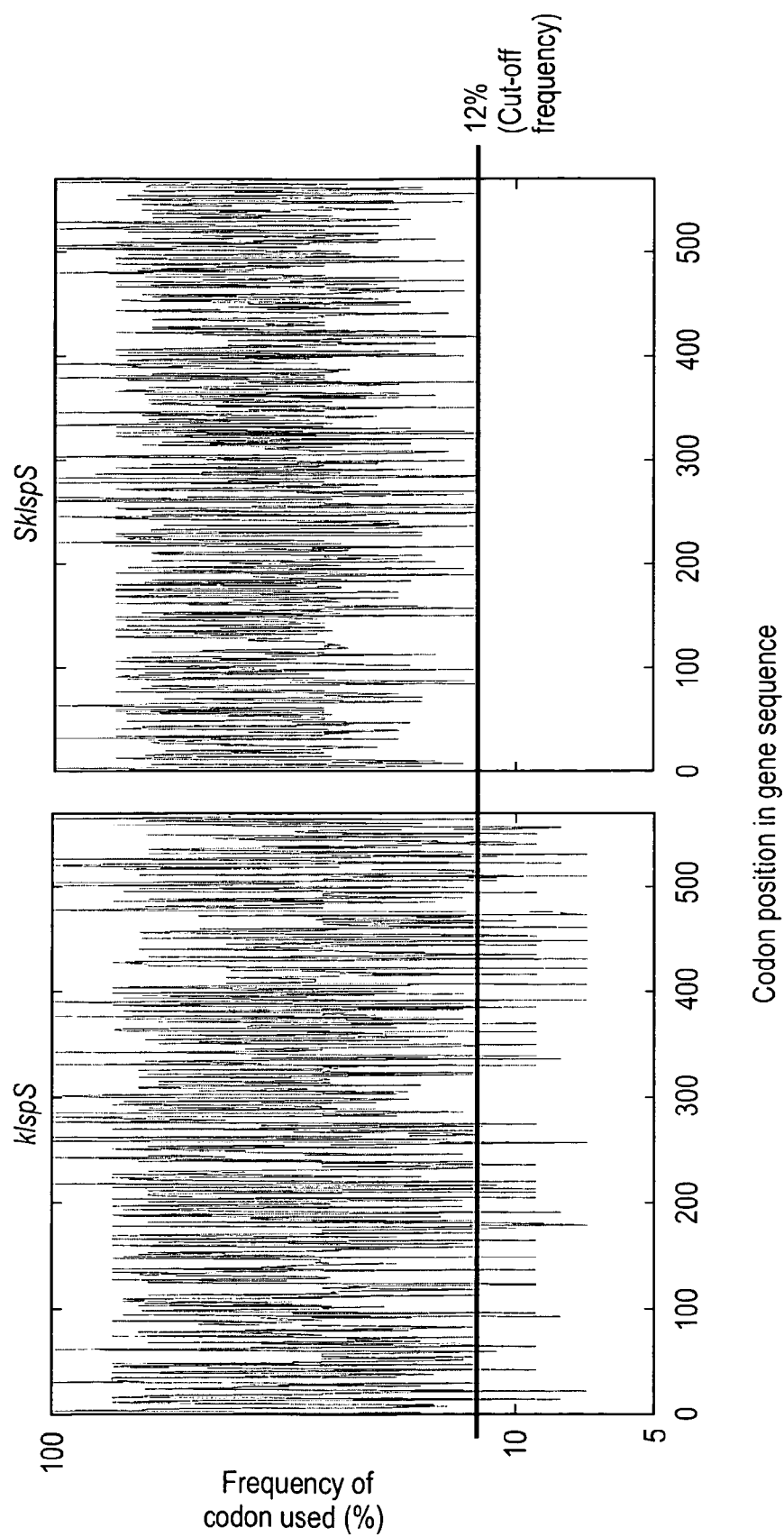
FIG. 3. Codon use adjustment for the IspS gene. Plot of the frequency of codons used for each position in the kIspS and SkIspS genes compared to a codon usage table derived from the genome sequence of *Synechocystis*. The 12% cut-off frequency used in the gene adjustment is shown as a horizontal line. Y-axis is plotted as the log of the frequency of codons used in order to emphasize the difference between the two sequences in regard to usage of rare codons.

Because the native kudzu cDNA sequence has a codon usage different from that preferred by *Synechocystis*, a de novo codon-adjusted version of the gene was designed and synthesized. In this adjusted version of the gene, referred to here as SkIspS, the codon usage was adapted to eliminate rare codons in the recipient host organism. Rare codons were first defined, using a codon usage table derived from the sequenced genome of *Synechocystis* (Nakamura et al. 2000). FIG. 3 presents a graphic illustration of the difference in codon usage between the original kIspS and the codon-adjusted SkIspS gene. It plots the predicted frequency of use of each IspS codon (kIspS or SkIspS) by *Synechocystis*. It is seen that, in the native kudzu IspS sequence (FIG. 3, kIspS), a substantial number of codons would be used with a frequency of less than 12% by *Synechocystis*. In the codon-adjusted gene (FIG. 3, SkIspS), codons that were to be used with an average frequency of less than 12% by *Synechocystis* were replaced by codons more frequently used. To test the effectiveness of codon-adjustment in the expression of the IspS gene, both the native kudzu sequence (kIspS), as well as the codon-adjusted SkIspS sequence were used for expression in *Synechocystis*.

Figure 4:
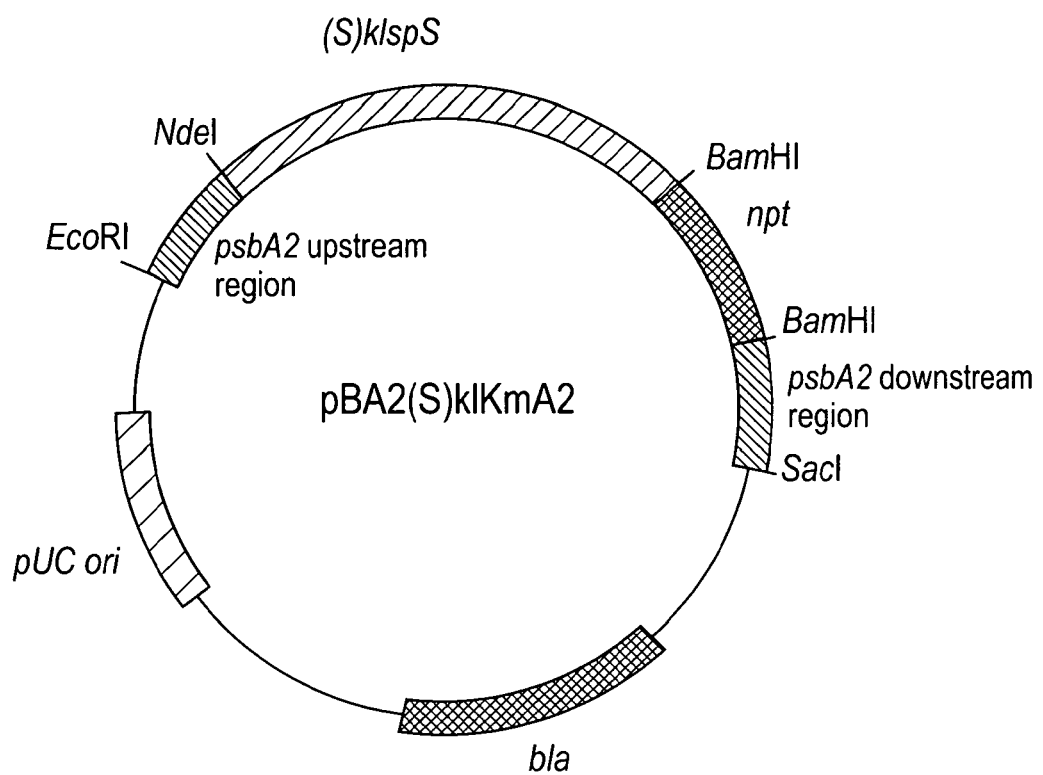
FIG. 4. Plasmid constructs for the transformation of *Synechocystis*. The two versions of the isoprene synthase gene, kIspS and SkIspS, were each cloned in a pBluescript-based plasmid, also containing the flanking sequences of psbA2 gene and an antibiotic resistance cassette, for double homologous recombination (insertion) into the *Synechocystis* genome. Restriction sites used for cloning are indicated. npt=neomycin phosphotransferase gene, conferring kanamycin resistance; bla=β-lactamase gene, conferring ampicillin resistance.
Figure 5A:
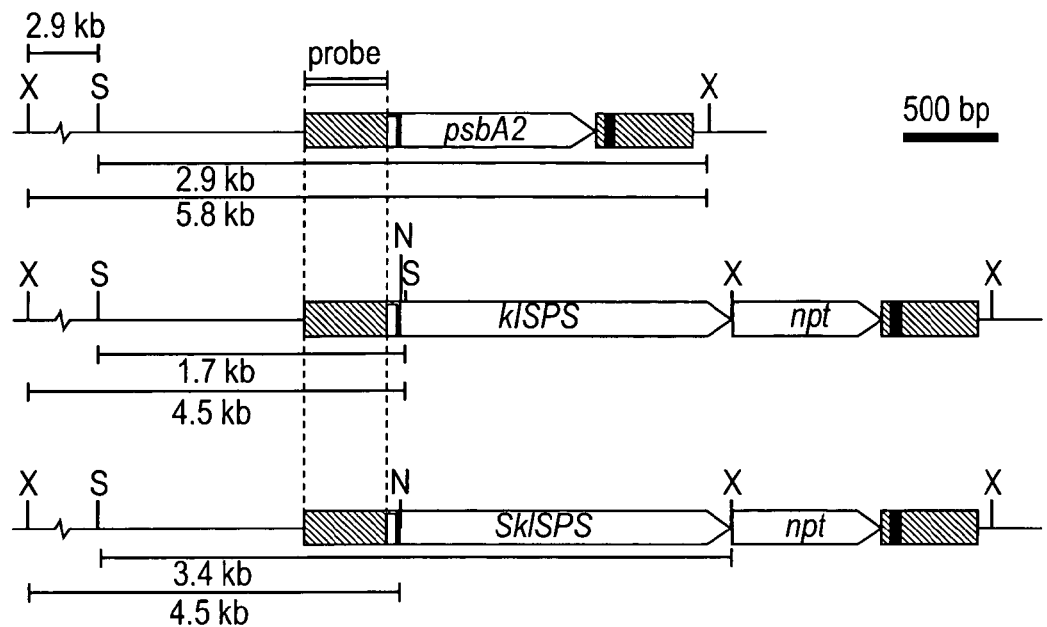
FIG. 5. Genetic maps and Southern blots of wild type and IspS transformants. (a) Map of the *Synechocystis* psbA2 locus, with the inserted kIspS and SkIspS genes, compared to the wild type. Restriction sites for XbaI (X), NdeI (N), and SacI (S) are indicated. Bars under each map show expected sizes of restriction fragments detected in Southern blots using the psbA2 upstream region probe ("probe"). (b) Southern blot on kIspS transformants and wild type *Synechocystis*. Left panel: restriction by XbaI and SacI. Right panel: Restriction by XbaI and NdeI. Lane 1: wild type; lane 2: kI-6; lane 2: kI-14; lane 3: kI-17. (c) Southern blot on SkISpS transformants and wild type *Synechocystis*. Left panel: restriction by XbaI and SacI. Right panel: Restriction by XbaI and NdeI. Lane 1: wild type; lane 2: kI-6; lane 2: kI-14; lane 3: kI-17.
Figure 5B:
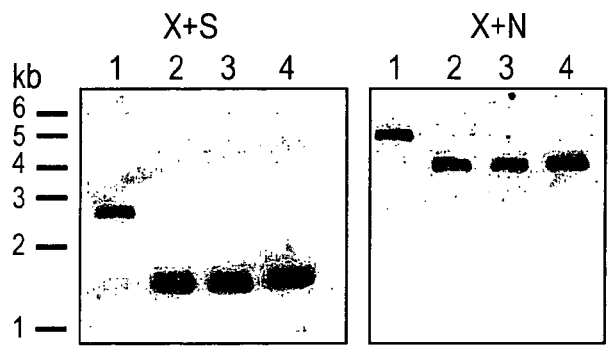

The two versions of the kudzu isoprene synthase gene, kIspS and SkIspS, each were cloned in a plasmid construct, where the respective gene was placed, together with an antibiotic resistance cassette, in-between the sequences immediately flanking the psbA2 gene in *Synechocystis* (FIG. 4). The resulting plasmids, containing kIspS or SkIspS, respectively, were used for double homologous recombination into the *Synechocystis* genomic DNA, yielding transformants whereby the psbA2 gene was replaced by kIspS or SkIspS, respectively (FIG. 5*a*). The correct insertion of the new genes into the *Synechocystis* circular DNA, and segregation of the transformed DNA copy from all wild type copies, was confirmed by PCR (not shown) and Southern hybridizations.

After subculturing of the transformant strains in selective media, no wild type copies of the *Synechocystis* DNA were detected by Southern hybridization to a specific probe (FIG. 5*a*, top map).

Figure 5C:
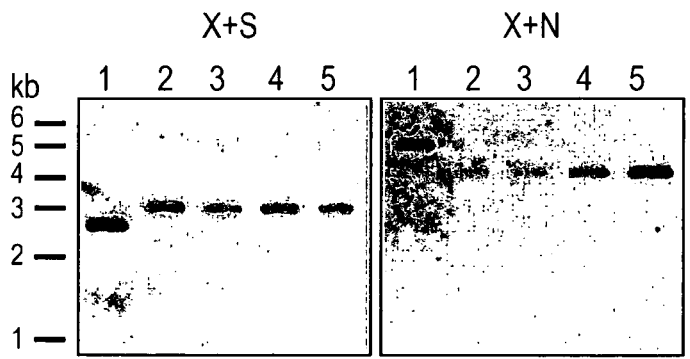

In the *Synechocystis* transformants carrying the SkIspS construct, digestion of the genomic DNA with SacI (S) and XbaI (X) (FIG. 5*a*, lower map) gave rise to a hybridization signal corresponding to a band of approximately 3.4 kb (FIG. 5*c*, left panel, lane 2-5), instead of the 2.9 kb fragment in the wild type. Conversely, when restriction enzymes XbaI (X) and NdeI (N) were employed in the digestion of the *Synechocystis* SkIspS transformants (FIG. 5*c*, right panel) genomic DNA fragments of approximately 4.5 kb in size were generated (FIG. 5*c*, right panel, lanes 2-5), instead of the 5.8 kb fragment in the wild type. This was due to the presence of an NdeI (N) restriction site in these transformants (FIG. 5*a*, lower map).

Fitness of the kIspS and SkIspS transformants, relative to that of the wild type, was tested by comparative measurements of the rate of growth, under conditions of limiting illumination at room temperature. Under such growth conditions, no significant growth differences could be detected between transformant strains and the wild type (results not shown), suggesting that transformation-expression of the IspS gene, and replacement of the psbA2 gene, did not adversely affect cell physiology and growth.

Figure 6A:
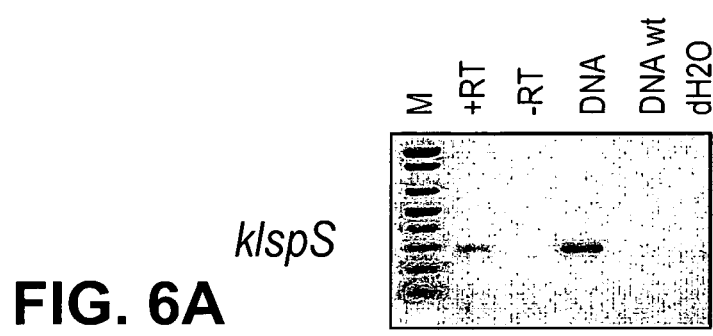
FIG. 6. RT-PCR results showing transcription of kIspS and SkIspS in transformed strains of *Synechocystis*. (a) Transcription of kIspS. Lanes are: M: molecular size markers; +RT: RT-PCR using RNA from kIspS strain 6 as template for the reverse transcription; −RT: as with +RT but without addition of RT enzyme in the reaction; DNA: positive control for the PCR using genomic DNA from kIspS strain 6 as template; DNA $dH_2O$: negative control for the PCR using water as template; DNA wt: negative control for the PCR using genomic DNA from wild type *Synechocystis* as template. (b) Transcription of SkIspS. Lanes are: +RT: RT-PCR using RNA from SkIspS strain 1.2 as template for the reverse transcription; −RT: as with +RT but without addition of RT enzyme in the reaction; DNA: positive control for the PCR using genomic DNA from SkIspS strain 1.2 as template; DNA wt: negative control for the PCR using genomic DNA from wild type *Synechocystis* as template; dH$_2$O: negative control for the PCR using water as template; M: molecular size markers.
Figure 6B:
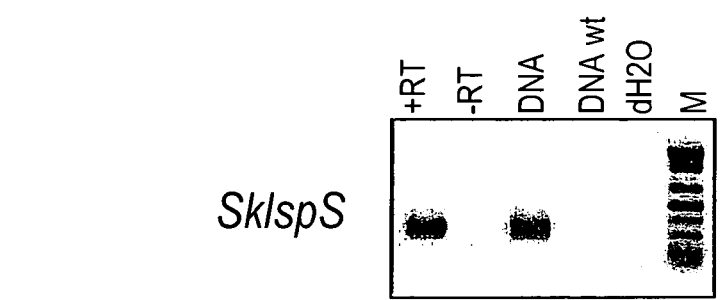

RT-PCR was employed to test whether the IspS genes, as cloned downstream of and in frame with the psbA2 promoter, were transcribed in *Synechocystis*. Cultures of wild type and transformant cell lines carrying the kIspS or SkIspS constructs were harvested in the exponential growth phase, and RNA extracted for analysis. The RT-PCR analysis showed that both versions of the gene (kIspS and SkIspS) were indeed expressed. This is shown in FIG. 6*a* (lane +RT) for kIspS and FIG. 6*b* (lane +RT) for SkIspS, where IspS amplification products were visualized on agarose gels, demonstrating the presence of kIspS and SkIspS mRNA in these different transformants. In control lanes (FIG. 6*a* and FIG. 6*b*, lanes marked by –RT, DNA wt, and dH$_2$O) i.e., when no RT enzyme was added, wild type DNA was used as template, or water was used instead of enzyme, no amplification products could be seen from the PCR reaction. Conversely, when genomic DNA was employed as a template in the PCR reaction (FIG. 6, DNA), a band of the same size as in the RT-PCR analysis (FIG. 6, +RT) was evident, both in the kIspS and SkIspS transformants.

Western blot analysis and immunodetection of the isoprene synthase enzyme, using specific polyclonal antibodies raised against the *E. coli*-expressed recombinant protein, confirmed the presence of the IspS protein in *Synechocystis* (FIG. 7*a*). The IspS is predicted to be a soluble protein (Sharkey et al., 2005, supra), and in agreement with this prediction, it was localized in the soluble fraction of *Synechocystis* whole cell extracts. FIG. 7*a*, wt control lane, shows absence of cross-reaction between the IspS polyclonal antibodies and any protein of the *Synechocystis* wild type soluble extract. FIG. 7*a*, lanes 1-3, show a specific cross-reaction between the IspS polyclonal antibodies and a protein band at about 65 kD from soluble extracts of three independent clone lines of *Synechocystis* transformants carrying the kIspS construct. A similar but stronger cross-reaction was detected between the IspS polyclonal antibodies and a protein band at about 65 kD from extracts of three independent clone lines of *Synechocystis* transformants carrying SkIspS construct (FIG. 7*a*, lanes 4-6). These results clearly show presence of the recombinant IspS protein in the *Synechocystis* transformants. Importantly, it was consistently observed that the level of the IspS protein present in the SkIspS transformants was substantially greater (by a factor of about 10) than that in the kIspS transformant lines (FIG. 7*a*), suggesting a substantial positive effect on gene expression and clearly shows a strong positive effect of the codon usage adjustment on the level of gene expression.

To test the efficacy of the psbA2 promoter on the expression of the IspS gene in *Synechocystis*, experiments were conducted whereby cultures of *Synechocystis* transformants, expressing the IspS gene, were subjected to a light-shift regimen, i.e., a shift from low light (10 µmol photons m$^{-2}$ s$^{-1}$) to high light (500 µmol photons m$^{-2}$ s$^{-1}$) growth conditions. It is known from previous studies of the psbA2 promoter that high light conditions enhance expression of the psbA2 gene (Mohamed and Jansson, *Plant Mol Biol* 13: 693-700, 1989). Accordingly, soluble extracts from samples of *Synechocystis* were collected between 0 h and 6 h after a shift from low-light to high-light conditions and were analyzed by Western blot analysis and immunodetection. Protein levels of the α subunit of ATP synthase (AtpA) served as a control of gene expression. FIG. 7*b* (top panel) shows that the expression of IspS gene was induced as a function of time under high light, steadily, with levels of the IspS protein increasing steadily between 0 and 6 h of high-light incubation. Contrary to this induction, expression levels of the control AtpA protein were stable and unaffected by the light intensity shift of the cultures (FIG. 7b, middle panel). These results demonstrate that the psbA2 promoter is able to regulate the expression of the heterologously expressed IspS gene in response to shifting light conditions. Accordingly, use of the psbA2 promoter under high light conditions is a highly effective tool for the overexpression of the IspS gene.

Example 2

Production of Isoprene

Figure 8:
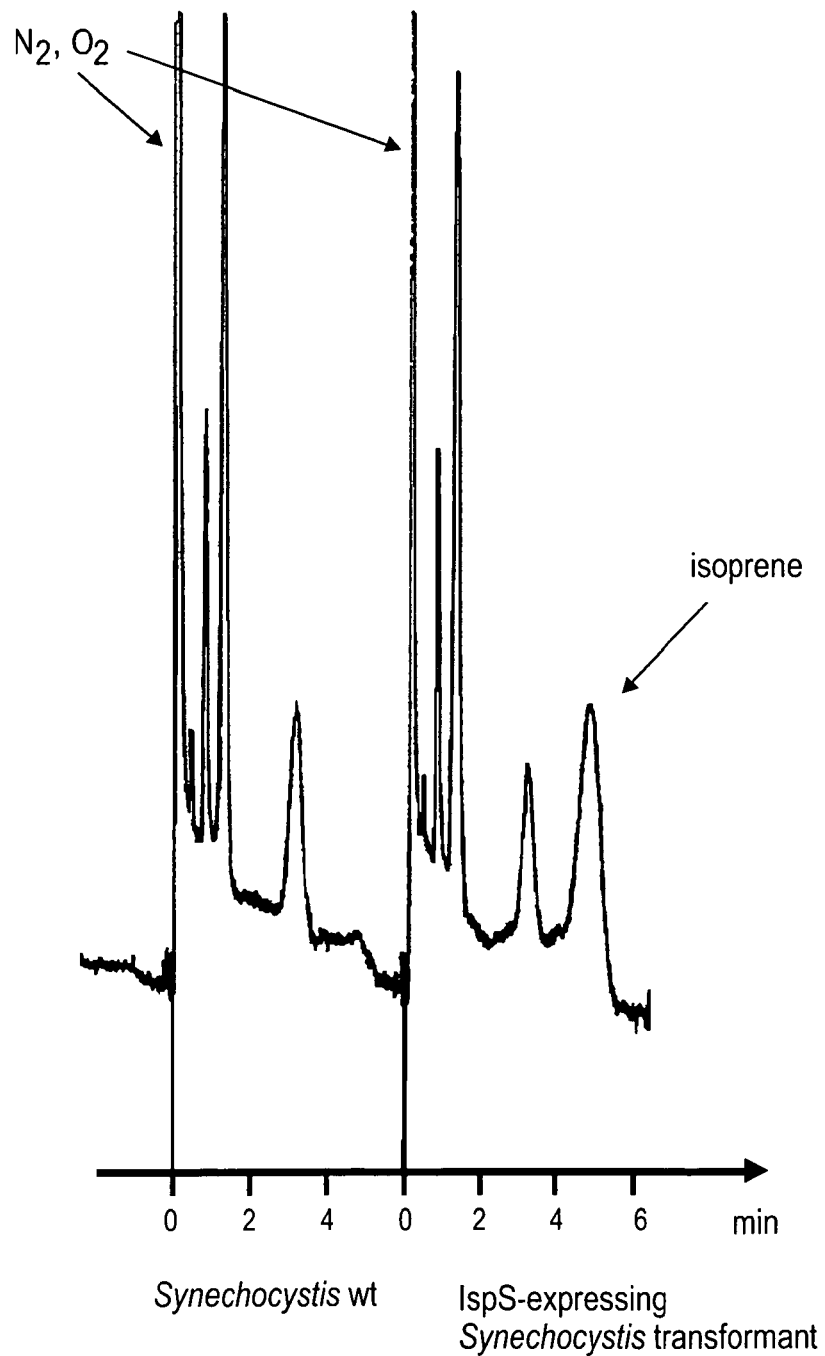
FIG. 8. Isoprene production measurements. An example of gas samples from the GC measurements is shown. Left panel: GC profile of a sample from the gas phase above a culture of *Synechocystis* wild type. Right panel: GC profile of a sample from the gas phase above a kIspS-expressing *Synechocystis* transformant culture. The isoprene peak is shown with an elution time of about 4-5 minutes.

The experiments in Example 1 demonstrated that *Synechocystis* and *E. coli* strains are amenable to heterologous transformation with the IspS gene, and that they express and accumulate the respective protein in their cytosol. To confirm that the expressed IspS protein is metabolically competent in these diverse bacteria, gas samples were obtained from the headspace of the cultures of wild type and IspS transformants and analyzed by suitable gas chromatography. In all such transformants, but not in their wild type counterparts, an isoprene peak was clearly evident, showing that the expressed enzyme is indeed active in the transformant strains. FIG. 8 shows an example of a comparative GC analysis of headspace gases from photosynthetically-grown *Synechocystis* wild type (left) and an IspS transformant (right), showing the isoprene peak at about 5 min after sample injection in the GC in the transformant but not in the wild type. The identity and quantity of isoprene represented by the observed peak was established by comparison with an isoprene standard.

The results demonstrate that isoprene was produced in cyanobacteria, e.g., *Synechocystis*, using a codon-adjusted kudzu plant. Rates of isoprene production with IspS transformed cyanobacterial cultures were (10% sunlight intensity) about 2 micrograms isoprene per liter culture per hour. Under 100% sunlight, rates were 40 micrograms isoprene per liter culture per hour. The cell density of the culture was OD730=~0.5, the chlorophyll concentration was about 1-2 mg/L, and dry cell biomass in the culture was 0.10-0.15 g/L.

Cyanobacteria were grown in minimal BG11 media supplemented with $CO_2$ in 1-liter cultures at 25° C., at a light intensity of approximately 100 μmol photons $m^{-2}$ $s^{-1}$ in the laboratory, or 2,000 μmol photons $m^{-2}$ $s^{-1}$ under direct sunlight. For selection and growth of transformed strains, 5 μg/ml of the antibiotic kanamycin was added to liquid BG11 medium. The cell density of the culture was minimally OD730=~0.5, and the chlorophyll concentration was minimally 1-2 mg/L. Rates of isoprene production with IspS transformed cyanobacterial cultures were (10% sunlight intensity) about 2 micrograms isoprene per liter culture per hour. Under 100% sunlight, rates were 20 micrograms isoprene per liter culture per hour.

In plasmid constructs employed for the expression of the isoprene synthase in *Synechocystis* in this work, we opted to use the psbA2 gene locus for the insertion of the transgenes. In doing so, the coding sequence of the psbA2 gene was replaced by the IspS gene, and the psbA2 promoter was used to drive expression of (S)kIspS. The gene psbA2 is one of three genes, the other two being psbA1 and psbA3, that encode the 32 kD/D1 reaction center protein of photosystem-II in *Synechocystis*. The promoter region and regulation of expression of the psbA2 gene has been well characterized (Eriksson et al., *Mol Cell Biol Res Commun* 3: 292-298, 2000; Mohamed et al., *Mol Gen Genet.* 238: 161-168, 1993; Mohamed and Jansson, *Plant Mol Biol* 13: 693-700, 1989). It has also been shown that a knock-out mutant in either psbA2 or psbA3 is able to grow photoautotrophically, as long as the other gene is still active, while psbA1 on its own was not able to compensate for the loss of both psbA2 and psbA3 (Mohamed and Jansson, 1989, supra). In this study we show that replacement of psbA2 gene by the IspS gene did not significantly affect normal photosynthesis and growth of the transformants and provided for highly effective expression of active IspS.

All publications, accession numbers, and patent applications cited in this specification are herein incorporated by reference as if each individual publication or patent application were specifically and individually indicated to be incorporated by reference.

Exemplary IspS Sequences

```
Pueraria montana var. lobata (kudzu vine) isoprene
synthase cDNA (kIspS gene) that encodes for the mature
protein (without the transit peptide). Start and stop
codons are indicated in bold font.
                                                SEQ ID NO: 1
ATGCCATGGCGAGTTATTTGTGCTACGAGCTCTCAATTTACCCAAATAACAGAAC

ATAATAGTCGGCGTTCAGCTAATTACCAGCCAAACCTCTGGAATTTTGAATTTCT

GCAGTCTCTGGAAAATGACCTTAAGGTGGAAAAACTAGAAGAGAAGGCAACAA

AGCTAGAGGAGGAGGTACGATGCATGATCAACAGAGTAGACACACAACCATTAA

GCTTACTAGAATTGATCGACGATGTCCAGCGTCTAGGATTGACCTACAAGTTTGA

GAAGGACATAATCAAAGCCCTTGAGAATATTGTTTTGCTGGATGAGAATAAGAA

AAATAAAAGTGACCTCCATGCTACTGCTCTCAGCTTCCGTTTACTTAGACAACAT

GGCTTTGAGGTTTCCCAAGATGTGTTTGAGAGATTTAAGGACAAGGAGGGAGGT

TTCAGTGGTGAACTTAAAGGTGATGTGCAAGGGTTGCTGAGTCTATATGAAGCAT

CCTATCTTGGCTTTGAGGGAGAAAATCTCTTGGAGGAGGCAAGGACATTTTCAAT

AACACATCTCAAGAACAACCTAAAAGAAGGAATAAACACCAAAGTGGCAGAAC

AAGTTAGTCATGCACTGGAACTTCCCTATCATCAAAGATTGCATAGACTAGAAGC
```

-continued

```
ACGATGGTTCCTTGACAAATATGAACCAAAGGAACCCCACCATCAGTTACTACTC

GAGCTTGCAAAGCTAGATTTCAATATGGTGCAAACATTGCACCAGAAAGAACTG

CAAGACCTGTCAAGGTGGTGGACGGAGATGGGGCTAGCAAGCAAGCTAGACTTT

GTCCGAGACAGATTAATGGAAGTGTATTTTTGGGCGTTGGGAATGGCACCTGATC

CTCAATTCGGTGAATGTCGTAAAGCTGTCACTAAAATGTTTGGATTGGTCACCAT

CATCGATGATGTATATGACGTTTATGGTACTTTGGATGAGCTACAACTCTTCACT

GATGCTGTTGAGAGATGGGACGTGAATGCCATAAACACACTTCCAGACTACATG

AAGTTGTGCTTCCTAGCACTTTATAACACCGTCAATGACACGTCTTATAGCATCCT

TAAAGAAAAAGGACACAACAACCTTTCCTATTTGACAAAATCTTGGCGTGAGTTA

TGCAAAGCATTCCTTCAAGAAGCAAAATGGTCGAACAACAAAATCATTCCAGCA

TTTAGCAAGTACCTGGAAAATGCATCGGTGTCCTCCTCCGGTGTGGCTTTGCTTG

CTCCTTCCTACTTCTCAGTGTGCCAACAACAAGAAGATATCTCAGACCATGCTCT

TCGTTCTTTAACTGATTTCCACGGCCTTGTGCGCTCCTCATGCGTCATTTTCAGAC

TCTGCAATGATTTGGCTACCTCAGCGGCTGAGCTAGAGAGGGGTGAGACGACAA

ATTCAATAATATCTTATATGCATGAGAATGACGGCACTTCTGAAGAGCAAGCACG

TGAGGAGTTGAGAAAATTGATCGATGCAGAGTGGAAGAAGATGAACCGAGAGC

GAGTTTCAGATTCTACACTACTCCCAAAAGCTTTTATGGAAATAGCTGTTAACAT

GGCTCGAGTTTCGCATTGCACATACCAATATGGAGACGGACTTGGAAGGCCAGA

CTACGCCACAGAGAATAGAATCAAGTTGCTACTTATAGACCCCTTTCCAATCAAT

CAACTAATGTACGTGTAA
```

*Pueraria montana* var. lobata (kudzu vine) mature isoprene synthase polypeptide sequence (lacking the transit peptide)

SEQ ID NO: 2

```
PWRVICATSSQFTQITEHNSRRSANYQPNLWNFEFLQSLENDLKVEKLEEKATKLEEE

VRCMINRVDTQPLSLLELIDDVQRLGLTYKFEKDIIKALENIVLLDENKKNKSDLHAT

ALSFRLLRQHGFEVSQDVFERFKDKEGGFSGELKGDVQGLLSLYEASYLGFEGENLL

EEARTFSITHLKNNLKEGINTKVAEQVSHALELPYHQRLHRLEARWFLDKYEPKEPH

HQLLLELAKLDFNMVQTLHQKELQDLSRWWTEMGLASKLDFVRDRLMEVYFWAL

GMAPDPQFGECRKAVTKMFGLVTIIDDVYDVYGTLDELQLFTDAVERWDVNAINTL

PDYMKLCFLALYNTVNDTSYSILKEKGHNNLSYLTKSWRELCKAFLQEAKWSNNKII

PAFSKYLENASVSSSGVALLAPSYFSVCQQQEDISDHALRSLTDFHGLVRSSCVIFRLC

NDLATSAAELERGETTNSIISYMHENDGTSEEQAREELRKLIDAEWKKMNRERVSDS

TLLPKAFMEIAVNMARVSHCTYQYGDGLGRPDYATENRIKLLLIDPFPINQLMYV
```

*Synechocystis*_PCC6803_optimized_kudzu IspS gene (S-k-IspS gene) encoding mature protein (lacking the transit peptide). Start and stop codons are indicated in bolded font. When transformed in cyanobacteria, this codon-optimized sequence was expressed at 10-20-times the level of the un-optimized native kudzu IspS sequence.

SEQ ID NO: 3

```
ATGCCCTGGCGTGTAATCTGTGCAACTTCTTCCCAATTTACTCAAATTACCGAGC

ACAATTCCCGGCGTAGTGCCAACTATCAACCCAATCTGTGGAACTTTGAGTTCTT

ACAGAGCCTGGAAAATGATTTAAAGGTCGAGAAATTGGAGGAGAAGGCCACTAA

ATTGGAAGAGGAAGTGCGGTGTATGATTAATCGTGTAGACACCCAACCATTGAG

TCTGTTAGAATTGATCGATGATGTGCAACGTCTCGGCCTGACATACAAATTCGAA

AAAGATATCATTAAGGCCCTAGAAAACATTGTCTTATTGGATGAAAACAAGAAA
```

AATAAGTCTGACTTGCATGCCACCGCTTTAAGTTTCCGCTTGTTGCGGCAGCACG

GCTTTGAAGTGTCCCAAGATGTTTTTGAACGGTTCAAAGACAAGGAGGGCGGCTT

TTCCGGCGAACTCAAAGGGGATGTTCAGGGCCTATTGTCTTTGTATGAAGCTAGT

TACTTGGGATTTGAAGGCGAGAATCTGTTAGAAGAAGCTCGCACTTTTTCCATTA

CACATTTAAAGAACAACCTAAAGGAAGGGATTAACACAAAAGTGGCTGAGCAGG

TGTCTCATGCTCTGGAGTTGCCGTATCATCAACGCTTACACCGGCTCGAAGCCCG

CTGGTTTTTGGATAAATATGAACCGAAAGAACCGCATCATCAATTACTGCTCGAA

CTGGCGAAGCTGGACTTTAATATGGTCCAAACACTACATCAGAAAGAACTCCAG

GACCTAAGTCGGTGGTGGACTGAAATGGGTCTGGCATCCAAGCTAGATTTTGTGC

GCGACCGTTTGATGGAGGTGTACTTCTGGGCACTAGGCATGGCTCCCGACCCGCA

GTTTGGTGAGTGTCGTAAGGCAGTGACCAAGATGTTTGGTTTAGTAACGATCATC

GACGACGTTTACGATGTCTATGGCACCCTAGACGAATTACAACTCTTTACAGATG

CCGTCGAACGTTGGGATGTTAATGCCATCAATACCTTACCTGATTACATGAAATT

GTGCTTCCTCGCCTTGTATAATACCGTTAATGACACCAGCTATTCTATTCTGAAGG

AAAAAGGCCACAATAACTTAAGCTACCTAACCAAAAGTTGGCGGGAATTGTGTA

AGGCTTTCTTACAGGAAGCCAAATGGTCCAACAACAAAATTATCCCCGCATTTTC

TAAATACCTGGAAAATGCCTCCGTGTCCTCTTCCGGGGTGGCTTTGCTAGCACCC

AGCTACTTTTCTGTTTGTCAGCAACAGGAGGACATCAGTGACCATGCCTTGCGGT

CCTTAACGGACTTTCATGGCTTAGTGCGGAGTAGCTGCGTCATTTTTCGTTTATGT

AACGATTTGGCTACAAGTGCTGCGGAATTGGAACGTGGGGAAACAACCAACAGC

ATTATCAGTTATATGCACGAAAACGATGGCACCAGTGAAGAGCAGGCACGGGAA

GAACTGCGCAAATTAATCGACGCTGAATGGAAGAAGATGAATCGCGAACGTGTG

TCTGATAGTACCTTATTACCTAAAGCCTTCATGGAAATTGCGGTGAATATGGCCC

GCGTCAGTCATTGCACTTACCAATACGGCGATGGATTAGGTCGGCCCGATTACGC

AACGGAAAATCGGATCAAATTGCTATTGATTGATCCGTTCCCAATTAATCAATTA

ATGTACGTGTAA

---

What is claimed is:

1. A method of producing isoprene hydrocarbons in a *cyanobacteria* sp., the method comprising:
    introducing an expression cassette that comprises a nucleic acid encoding an isoprene synthase (IspS) into the *cyanobacteria* sp., to obtain cyanobacteria comprising the nucleic acid, wherein the nucleic acid encoding isoprene synthase is codon optimized and is operably linked to a psbA2 promoter, and further wherein the nucleic acid has at least 90% identity to the region of SEQ ID NO:3 that encodes the IspS;
    culturing the cyanobacteria under conditions to achieve DNA homoplasmy; and
    culturing the cyanobacteria under conditions in which the nucleic acid encoding isoprene synthase is expressed.

2. The method of claim 1, wherein the expression cassette is introduced into the PsbA2 gene locus and the PsbA2 promoter is the native cyanobacteria promoter.

3. The method of claim 1, wherein the cyanobacteria are cultured under conditions in which expression of isoprene synthase is responsive to light intensity.

4. The method of claim 3, wherein the cyanobacteria are cultured at a light intensity of about 50 μmol photons $m^{-2} s^{-1}$ to about 2,500 μmol photons $m^{-2} s^{-1}$.

5. The method of claim 1, wherein the *cyanobacteria* sp. is unicellular.

6. The method of claim 1, wherein the nucleic acid is a codon-adjusted variant of SEQ ID NO:1 where codons used with an average frequency of less than 12% by *Synechocystis* are replaced by more frequently used codons.

7. The method of claim 1, wherein the isoprene synthase nucleic acid comprises SEQ ID NO:3.

8. A method of producing isoprene hydrocarbons in a cyanobacteria that comprises a heterologous nucleic acid, the method comprising:
    mass-culturing a cyanobacteria cell population obtained in accordance with the method of claim 1 in an enclosed bioreactor under conditions in which the isoprene synthase is expressed; and
    harvesting volatile isoprene hydrocarbons produced by the cyanobacteria.

9. The method of claim 8 wherein the cyanobacteria is a unicellular *cyanobacteria* sp.

10. The method of claim 8, wherein the cyanobacterial cell population is mass-cultured in the absence of antibiotics.

11. The method of claim 8, wherein the expression cassette is introduced into the PsbA2 gene locus and the PsbA2 promoter is the native cyanobacteria promoter.

12. The method of claim 8, wherein the cyanobacteria are cultured under conditions in which expression of the isoprene synthase is responsive to light intensity.

13. The method of claim 12, wherein the cyanobacteria are cultured at a light intensity of about 50 μmol photons $m^{-2} s^{-1}$ to about 2,500 μmol photons $m^{-2} s^{-1}$.

14. The method of claim 8, wherein the nucleic acid encodes an isoprene synthase that comprises amino acid sequence SEQ ID NO:2.

15. The method of claim 14, wherein the nucleic acid is a codon-adjusted variant of SEQ ID NO:1 where codons used with an average frequency of less than 12% by *Synechocystis* are replaced by more frequently used codons.

16. The method of claim 15, wherein the isoprene synthase nucleic acid comprises SEQ ID NO:3.

* * * * *

SEQUENCE LISTING

<160> NUMBER OF SEQ ID NOS: 20

<210> SEQ ID NO 1
<211> LENGTH: 1710
<212> TYPE: DNA
<213> ORGANISM: Pueraria montana
<220> FEATURE:
<223> OTHER INFORMATION: Pueraria montana var. lobata kudzu vine
      isoprene synthase (kIspS) DNA encoding mature protein without
      transit peptide

<400> SEQUENCE: 1

```
atgccatggc gagttatttg tgctacgagc tctcaattta cccaaataac agaacataat      60
agtcggcgtt cagctaatta ccagccaaac ctctggaatt ttgaatttct gcagtctctg     120
gaaaatgacc ttaaggtgga aaaactagaa gagaaggcaa caaagctaga ggaggagta     180 cgatgcatga tcaacagagt agacacacaa ccattaagct tactagaatt gatcgacgat     240
gtccagcgtc taggattgac ctacaagttt gagaaggaca taatcaaagc ccttgagaat     300
```

```
attgttttgc tggatgagaa taagaaaaat aaaagtgacc tccatgctac tgctctcagc      360
ttccgtttac ttagacaaca tggctttgag gtttcccaag atgtgtttga gagatttaag      420
gacaaggagg gaggtttcag tggtgaactt aaaggtgatg tgcaagggtt gctgagtcta      480
tatgaagcat cctatcttgg ctttgaggga gaaaatctct tggaggaggc aaggacattt      540
tcaataacac atctcaagaa caacctaaaa gaaggaataa acaccaaagt ggcagaacaa      600
gttagtcatg cactggaact tccctatcat caaagattgc atagactaga agcacgatgg      660
ttccttgaca aatatgaacc aaaggaaccc caccatcagt tactactcga gcttgcaaag      720
ctagatttca atatggtgca acattgcac cagaaagaac tgcaagacct gtcaaggtgg      780
tggacggaga tggggctagc aagcaagcta gactttgtcc gagacagatt aatggaagtg      840
tatttttggg cgttgggaat ggcacctgat cctcaattcg gtgaatgtcg taaagctgtc      900
actaaaatgt ttggattggt caccatcatc gatgatgtat atgacgttta tggtactttg      960
gatgagctac aactcttcac tgatgctgtt gagagatggg acgtgaatgc cataaacaca     1020
cttccagact acatgaagtt gtgcttccta gcactttata acaccgtcaa tgacacgtct     1080
tatagcatcc ttaaagaaaa aggacacaac aaccttcct atttgacaaa atcttggcgt      1140
gagttatgca aagcattcct tcaagaagca aaatggtcga acaacaaaat cattccagca     1200
tttagcaagt acctggaaaa tgcatcggtg tcctcctccg gtgtggcttt gcttgctcct     1260
tcctacttct cagtgtgcca acaacaagaa gatatctcag accatgctct tcgttcttta     1320
actgatttcc acggccttgt gcgctcctca tgcgtcattt tcagactctg caatgatttg     1380
gctacctcag cggctgagct agagaggggt gagacgacaa attcaataat atcttatatg     1440
catgagaatg acggcacttc tgaagagcaa gcacgtgagg agttgagaaa attgatcgat     1500
gcagagtgga agaagatgaa ccgagagcga gtttcagatt ctacactact cccaaaagct     1560
tttatggaaa tagctgttaa catggctcga gttcgcatt gcacatacca atatggagac      1620
ggacttggaa ggccagacta cgccacagag aatagaatca agttgctact tatagacccc     1680
tttccaatca atcaactaat gtacgtgtaa                                       1710
```

<210> SEQ ID NO 2
<211> LENGTH: 568
<212> TYPE: PRT
<213> ORGANISM: Pueraria montana
<220> FEATURE:
<223> OTHER INFORMATION: Pueraria montana var. lobata kudzu vine
      isoprene synthase (kIspS) mature protein without transit peptide

<400> SEQUENCE: 2

Pro Trp Arg Val Ile Cys Ala Thr Ser Ser Gln Phe Thr Gln Ile Thr
1               5                   10                  15

Glu His Asn Ser Arg Arg Ser Ala Asn Tyr Gln Pro Asn Leu Trp Asn
            20                  25                  30

Phe Glu Phe Leu Gln Ser Leu Glu Asn Asp Leu Lys Val Glu Lys Leu
        35                  40                  45

Glu Glu Lys Ala Thr Lys Leu Glu Glu Glu Val Arg Cys Met Ile Asn
    50                  55                  60

Arg Val Asp Thr Gln Pro Leu Ser Leu Leu Glu Leu Ile Asp Asp Val
65                  70                  75                  80

Gln Arg Leu Gly Leu Thr Tyr Lys Phe Glu Lys Asp Ile Ile Lys Ala
                85                  90                  95

Leu Glu Asn Ile Val Leu Leu Asp Glu Asn Lys Lys Asn Lys Ser Asp

```
            100                 105                 110
Leu His Ala Thr Ala Leu Ser Phe Arg Leu Leu Arg Gln His Gly Phe
            115                 120                 125

Glu Val Ser Gln Asp Val Phe Glu Arg Phe Lys Asp Lys Glu Gly Gly
130                 135                 140

Phe Ser Gly Glu Leu Lys Gly Asp Val Gln Gly Leu Leu Ser Leu Tyr
145                 150                 155                 160

Glu Ala Ser Tyr Leu Gly Phe Glu Gly Glu Asn Leu Leu Glu Glu Ala
                    165                 170                 175

Arg Thr Phe Ser Ile Thr His Leu Lys Asn Asn Leu Lys Glu Gly Ile
                    180                 185                 190

Asn Thr Lys Val Ala Glu Gln Val Ser His Ala Leu Glu Leu Pro Tyr
            195                 200                 205

His Gln Arg Leu His Arg Leu Glu Ala Arg Trp Phe Leu Asp Lys Tyr
            210                 215                 220

Glu Pro Lys Glu Pro His His Gln Leu Leu Leu Glu Leu Ala Lys Leu
225                 230                 235                 240

Asp Phe Asn Met Val Gln Thr Leu His Gln Lys Glu Leu Gln Asp Leu
                    245                 250                 255

Ser Arg Trp Trp Thr Glu Met Gly Leu Ala Ser Lys Leu Asp Phe Val
                    260                 265                 270

Arg Asp Arg Leu Met Glu Val Tyr Phe Trp Ala Leu Gly Met Ala Pro
            275                 280                 285

Asp Pro Gln Phe Gly Glu Cys Arg Lys Ala Val Thr Lys Met Phe Gly
            290                 295                 300

Leu Val Thr Ile Ile Asp Asp Val Tyr Asp Val Tyr Gly Thr Leu Asp
305                 310                 315                 320

Glu Leu Gln Leu Phe Thr Asp Ala Val Glu Arg Trp Asp Val Asn Ala
                    325                 330                 335

Ile Asn Thr Leu Pro Asp Tyr Met Lys Leu Cys Phe Leu Ala Leu Tyr
                    340                 345                 350

Asn Thr Val Asn Asp Thr Ser Tyr Ser Ile Leu Lys Glu Lys Gly His
            355                 360                 365

Asn Asn Leu Ser Tyr Leu Thr Lys Ser Trp Arg Glu Leu Cys Lys Ala
370                 375                 380

Phe Leu Gln Glu Ala Lys Trp Ser Asn Asn Lys Ile Ile Pro Ala Phe
385                 390                 395                 400

Ser Lys Tyr Leu Glu Asn Ala Ser Val Ser Ser Gly Val Ala Leu
                    405                 410                 415

Leu Ala Pro Ser Tyr Phe Ser Val Cys Gln Gln Glu Asp Ile Ser
                    420                 425                 430

Asp His Ala Leu Arg Ser Leu Thr Asp Phe His Gly Leu Val Arg Ser
            435                 440                 445

Ser Cys Val Ile Phe Arg Leu Cys Asn Asp Leu Ala Thr Ser Ala Ala
            450                 455                 460

Glu Leu Glu Arg Gly Glu Thr Thr Asn Ser Ile Ile Ser Tyr Met His
465                 470                 475                 480

Glu Asn Asp Gly Thr Ser Glu Glu Gln Ala Arg Glu Glu Leu Arg Lys
                    485                 490                 495

Leu Ile Asp Ala Glu Trp Lys Lys Met Asn Arg Glu Arg Val Ser Asp
                    500                 505                 510

Ser Thr Leu Leu Pro Lys Ala Phe Met Glu Ile Ala Val Asn Met Ala
            515                 520                 525
```

Arg Val Ser His Cys Thr Tyr Gln Tyr Gly Asp Gly Leu Gly Arg Pro
                530                 535                 540

Asp Tyr Ala Thr Glu Asn Arg Ile Lys Leu Leu Leu Ile Asp Pro Phe
545                 550                 555                 560

Pro Ile Asn Gln Leu Met Tyr Val
                565

<210> SEQ ID NO 3
<211> LENGTH: 1710
<212> TYPE: DNA
<213> ORGANISM: Artificial Sequence
<220> FEATURE:
<223> OTHER INFORMATION: synthetic cyanobacteria Synechocystis PCC6803
      codon-optimized Pueraria montana var. lobata kudzu
      vine isoprene synthase (kIspS) DNA encoding mature
      protein without transit peptide

<400> SEQUENCE: 3

```
atgccctggc gtgtaatctg tgcaacttct tcccaattta ctcaaattac cgagcacaat      60
tcccggcgta gtgccaacta tcaacccaat ctgtggaact ttgagttctt acagagcctg    120
gaaaatgatt taaaggtcga gaaattggag gagaaggcca ctaaattgga agaggaagtg    180
cggtgtatga ttaatcgtgt agacacccaa ccattgagtc tgttagaatt gatcgatgat    240
gtgcaacgtc tcggcctgac atacaaattc gaaaaagata tcattaaggc cctagaaaac    300
attgtcttat tggatgaaaa caagaaaaat aagtctgact tgcatgccac cgctttaagt    360
ttccgcttgt tgcggcagca cggctttgaa gtgtcccaag atgttttttga acggttcaaa    420
gacaaggagg gcggcttttc cggcgaactc aaaggggatg ttcagggcct attgtctttg    480
tatgaagcta gttacttggg atttgaaggc gagaatctgt tagaagaagc tcgcactttt    540
tccattacac atttaaagaa caacctaaag gaagggatta acacaaaagt ggctgagcag    600
gtgtctcatg ctctggagtt gccgtatcat caacgcttac accggctcga agcccgctgg    660
tttttggata aatatgaacc gaaagaaccg catcatcaat tactgctcga actggcgaag    720
ctggacttta atatggtcca aacactacat cagaaagaac tccaggacct aagtcggtgg    780
tggactgaaa tgggtctggc atccaagcta gattttgtgc gcgaccgttt gatggaggtg    840
tacttctggg cactaggcat ggctcccgac ccgcagtttg tgagtgtcg taaggcagtg    900
accaagatgt ttggtttagt aacgatcatc gacgacgttt acgatgtcta tggcacccta    960
gacgaattac aactctttac agatgccgtc gaacgttggg atgttaatgc catcaatacc   1020
ttacctgatt acatgaaatt gtgcttcctc gccttgtata ataccgttaa tgacaccagc   1080
tattctattc tgaaggaaaa aggccacaat aacttaagct acctaaccaa agttggcgg   1140
gaattgtgta aggctttctt acaggaagcc aaatggtcca caacaaaat tatccccgca   1200
ttttctaaat acctggaaaa tgcctccgtg tcctcttccg gggtggcttt gctagcaccc   1260
agctactttt ctgtttgtca gcaacaggag gacatcagtg accatgcctt gcggtcctta   1320
acggactttc atggcttagt gcggagtagc tgcgtcattt ttcgtttatg taacgatttg   1380
gctacaagtg ctgcggaatt ggaacgtggg gaaacaacca acagcattat cagttatatg   1440
cacgaaaacg atggcaccag tgaagagcag gcacgggaag aactgcgcaa attaatcgac   1500
gctgaatgga gaagatgaa tcgcgaacgt gtgtctgata gtaccttatt acctaaagcc   1560
ttcatggaaa ttgcggtgaa tatggcccgc gtcagtcatt gcacttacca atacggcgat   1620
ggattaggtc ggcccgatta cgcaacggaa atcggatcaa aattgctatt gattgatccg   1680
```
ttcccaatta atcaattaat gtacgtgtaa                                      1710

<210> SEQ ID NO 4
<211> LENGTH: 27
<212> TYPE: DNA
<213> ORGANISM: Artificial Sequence
<220> FEATURE:
<223> OTHER INFORMATION: synthetic PCR amplification primer A2us_Eco_F
      for psbA2 gene upstream region

<400> SEQUENCE: 4
gagagagaat tcagcgttcc agtggat                                         27

<210> SEQ ID NO 5
<211> LENGTH: 30
<212> TYPE: DNA
<213> ORGANISM: Artificial Sequence
<220> FEATURE:
<223> OTHER INFORMATION: synthetic PCR amplification primer
      A2us_NdeI_Bam_R for psbA2 gene upstream region

<400> SEQUENCE: 5
gttggatccg tcgttgtcat atggttataa                                      30

<210> SEQ ID NO 6
<211> LENGTH: 27
<212> TYPE: DNA
<213> ORGANISM: Artificial Sequence
<220> FEATURE:
<223> OTHER INFORMATION: synthetic PCR amplification primer A2ds_Bam_F
      for psbA2 gene downstream region

<400> SEQUENCE: 6
gagagagagg atccttggtg taatgcc                                         27

<210> SEQ ID NO 7
<211> LENGTH: 33
<212> TYPE: DNA
<213> ORGANISM: Artificial Sequence
<220> FEATURE:
<223> OTHER INFORMATION: synthetic PCR amplification primer A2ds_SacI_R
      for psbA2 gene downstream region

<400> SEQUENCE: 7
gagagagaga gctcgatcgc cttggcaaaa caa                                  33

<210> SEQ ID NO 8
<211> LENGTH: 20
<212> TYPE: DNA
<213> ORGANISM: Artificial Sequence
<220> FEATURE:
<223> OTHER INFORMATION: synthetic RT-PCR amplification gene-specific
      primer RT_kIspS_F for kIspS

<400> SEQUENCE: 8
tcttggcttt gagggagaaa                                                 20

<210> SEQ ID NO 9
<211> LENGTH: 20
<212> TYPE: DNA
<213> ORGANISM: Artificial Sequence
<220> FEATURE:
<223> OTHER INFORMATION: synthetic RT-PCR amplification gene-specific
      primer RT_kIspS_R for kIspS

<400> SEQUENCE: 9
ccaccacctt gacaggtctt                                                 20

<210> SEQ ID NO 10
<211> LENGTH: 20
<212> TYPE: DNA
<213> ORGANISM: Artificial Sequence
<220> FEATURE:
<223> OTHER INFORMATION: synthetic RT-PCR amplification gene-specific
      primer RT_SkIspS_F for SkIspS

<400> SEQUENCE: 10
cggtccttaa cggactttca                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic RT-PCR amplification gene-specific
      primer RT_SkIspS_R for SkIspS

<400> SEQUENCE: 11
atcgccgtat tggtaagtgc                                              20

<210> SEQ ID NO 12
<211> LENGTH: 20
<212> TYPE: DNA
<213> ORGANISM: Artificial Sequence
<220> FEATURE:
<223> OTHER INFORMATION: synthetic RT-PCR amplification gene-specific
      primer RT_rbcL_F for positive control rcbL

<400> SEQUENCE: 12
gtatcaccat gggcttcgtt                                              20

<210> SEQ ID NO 13
<211> LENGTH: 20
<212> TYPE: DNA
<213> ORGANISM: Artificial Sequence
<220> FEATURE:
<223> OTHER INFORMATION: synthetic RT-PCR amplification gene-specific
      primer RT_rbcL_R for positive control rcbL

<400> SEQUENCE: 13
cacaagcttc caaagcaaca                                              20

<210> SEQ ID NO 14
<211> LENGTH: 26
<212> TYPE: DNA
<213> ORGANISM: Artificial Sequence
<220> FEATURE:
<223> OTHER INFORMATION: synthetic PCR amplification primer A2us_probe_R
      for generation of Synechocystis genomic DNA probe

<400> SEQUENCE: 14
gagttttgta aagctttgta acagga                                       26

<210> SEQ ID NO 15
<211> LENGTH: 27
<212> TYPE: DNA
<213> ORGANISM: Artificial Sequence
<220> FEATURE:
<223> OTHER INFORMATION: synthetic PCR amplification primer A2us_Eco_F
      for generation of Synechocystis genomic DNA probe

<400> SEQUENCE: 15
gagagagaat tcagcgttcc agtggat                                      27

-continued

```
<210> SEQ ID NO 16
<211> LENGTH: 6
<212> TYPE: PRT
<213> ORGANISM: Artificial Sequence
<220> FEATURE:
<223> OTHER INFORMATION: synthetic 6xHis-tag epitope

<400> SEQUENCE: 16

His His His His His His
 1               5

<210> SEQ ID NO 17
<211> LENGTH: 595
<212> TYPE: PRT
<213> ORGANISM: Populus alba
<220> FEATURE:
<223> OTHER INFORMATION: white poplar isoprene synthase (IspS)

<400> SEQUENCE: 17

Met Ala Thr Glu Leu Leu Cys Leu His Arg Pro Ile Ser Leu Thr His
 1               5                  10                  15

Lys Leu Phe Arg Asn Pro Leu Pro Lys Val Ile Gln Ala Thr Pro Leu
             20                  25                  30

Thr Leu Lys Leu Arg Cys Ser Val Ser Thr Glu Asn Val Ser Phe Thr
         35                  40                  45

Glu Thr Glu Thr Glu Ala Arg Arg Ser Ala Asn Tyr Glu Pro Asn Ser
     50                  55                  60

Trp Asp Tyr Asp Tyr Leu Leu Ser Ser Asp Thr Asp Glu Ser Ile Glu
 65                  70                  75                  80

Val Tyr Lys Asp Lys Ala Lys Lys Leu Glu Ala Glu Val Arg Arg Glu
                 85                  90                  95

Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Gly Ala Leu Asp Arg Phe Val Ser Ser Gly Gly Phe Asp Ala Val Thr
    130                 135                 140

Lys Thr Ser Leu His Gly Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Ile Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Lys Val Phe Ala Ile Ser His Leu Lys Glu Leu Ser Glu
    210                 215                 220

Glu Lys Ile Gly Lys Glu Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
            260                 265                 270

Ala Ile Leu Asp Tyr Asn Met Ile Gln Ser Val Tyr Gln Arg Asp Leu
        275                 280                 285

Arg Glu Thr Ser Arg Trp Trp Arg Arg Val Gly Leu Ala Thr Lys Leu
    290                 295                 300
```

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
                340                 345                 350

Thr Leu Asp Glu Leu Glu Leu Phe Thr Asp Ala Val Glu Arg Trp Asp
                355                 360                 365

Val Asn Ala Ile Asn Asp Leu Pro Asp Tyr Met Lys Leu Cys Phe Leu
370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
                420                 425                 430

Pro Thr Phe Asp Asp Tyr Phe Gly Asn Ala Trp Lys Ser Ser Ser Gly
                435                 440                 445

Pro Leu Gln Leu Val Phe Ala Tyr Phe Ala Val Gln Asn Ile Lys
                450                 455                 460

Lys Glu Glu Ile Glu Asn Leu Gln Lys Tyr His Asp Thr Ile Ser Arg
465                 470                 475                 480

Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
                500                 505                 510

Thr Lys Gly Ile Ser Glu Glu Leu Ala Thr Glu Ser Val Met Asn Leu
                515                 520                 525

Ile Asp Glu Thr Trp Lys Lys Met Asn Lys Glu Lys Leu Gly Gly Ser
530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
                580                 585                 590

Phe Glu Arg
        595

<210> SEQ ID NO 18
<211> LENGTH: 595
<212> TYPE: PRT
<213> ORGANISM: Populus tremuloides
<220> FEATURE:
<223> OTHER INFORMATION: quaking aspen isoprene synthase (IspS)

<400> SEQUENCE: 18

Met Ala Thr Glu Leu Leu Cys Leu His Arg Pro Ile Ser Leu Thr His
1               5                   10                  15

Lys Leu Phe Arg Asn Pro Leu Pro Lys Val Ile Gln Ala Thr Pro Leu
                20                  25                  30

Thr Leu Lys Leu Arg Cys Ser Val Ser Thr Glu Asn Val Ser Phe Ser
            35                  40                  45

Glu Thr Glu Thr Glu Thr Arg Arg Ser Ala Asn Tyr Glu Pro Asn Ser
50                  55                  60

-continued

```
Trp Asp Tyr Asp Tyr Leu Leu Ser Ser Asp Thr Asp Glu Ser Ile Glu
 65                  70                  75                  80

Val His Lys Asp Lys Ala Lys Lys Leu Glu Ala Glu Val Arg Arg Glu
                 85                  90                  95

Ile Asn Asn Glu Lys Ala Glu Phe Leu Thr Leu Leu Gly Leu Ile Asp
                100                 105                 110

Asn Val Gln Arg Leu Gly Leu Gly Tyr Arg Phe Glu Ser Asp Ile Arg
                115                 120                 125

Arg Ala Leu Asp Arg Phe Val Ser Ser Gly Gly Phe Asp Gly Val Thr
                130                 135                 140

Lys Thr Ser Leu His Gly Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Ile Lys Ala Ile Leu
                180                 185                 190

Ser Leu Tyr Glu Ala Ser Phe Leu Ala Leu Glu Gly Glu Asn Ile Leu
                195                 200                 205

Asp Glu Ala Lys Val Phe Ala Ile Ser His Leu Lys Glu Leu Ser Glu
                210                 215                 220

Glu Lys Ile Gly Lys Glu Leu Ala Glu Gln Val Ser His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
                260                 265                 270

Ala Ile Leu Asp Tyr Asn Met Ile Gln Ser Val Tyr Gln Arg Asp Leu
                275                 280                 285

Arg Glu Thr Ser Arg Trp Trp Arg Arg Val Gly Leu Ala Thr Lys Leu
                290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
                340                 345                 350

Thr Leu Asp Glu Leu Glu Leu Phe Thr Asp Ala Val Glu Arg Trp Asp
                355                 360                 365

Val Asn Ala Ile Asn Asp Leu Pro Asp Tyr Met Lys Leu Cys Phe Leu
                370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
                420                 425                 430

Pro Thr Phe Asp Asp Tyr Phe Gly Asn Ala Trp Lys Ser Ser Ser Gly
                435                 440                 445

Pro Leu Gln Leu Ile Phe Ala Tyr Phe Ala Val Val Gln Asn Ile Lys
                450                 455                 460

Lys Glu Glu Ile Glu Asn Leu Gln Lys Tyr His Asp Ile Ile Ser Arg
465                 470                 475                 480
```

```
Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
        500                 505                 510

Thr Lys Gly Ile Ser Glu Glu Leu Ala Thr Glu Ser Val Met Asn Leu
            515                 520                 525

Ile Asp Glu Thr Trp Lys Lys Met Asn Lys Glu Lys Leu Gly Gly Ser
        530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
        595

<210> SEQ ID NO 19
<211> LENGTH: 595
<212> TYPE: PRT
<213> ORGANISM: Populus nigra
<220> FEATURE:
<223> OTHER INFORMATION: Lombardy poplar isoprene synthase (IspS)

<400> SEQUENCE: 19

Met Ala Thr Glu Leu Leu Cys Leu His Arg Pro Ile Ser Leu Thr His
1               5                   10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Thr Glu Thr Arg Arg Ser Ala Asn Tyr Glu Pro Asn Ser
    50                  55                  60

Trp Asp Tyr Asp Tyr Leu Leu Ser Ser Asp Thr Asp Glu Ser Ile Glu
65                  70                  75                  80

Val Tyr Lys Asp Lys Ala Lys Lys Leu Glu Ala Glu Val Arg Arg Glu
                85                  90                  95

Ile Asn Asn Glu Lys Ala Glu Phe Leu Thr Leu Pro Glu Leu Ile Asp
            100                 105                 110

Asn Val Gln Arg Leu Gly Leu Gly Tyr Arg Phe Glu Ser Asp Ile Arg
        115                 120                 125

Arg Ala Leu Asp Arg Phe Val Ser Ser Gly Gly Phe Asp Ala Val Thr
    130                 135                 140

Lys Thr Ser Leu His Ala Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Lys Asn Leu Lys Glu Asp Ile Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Lys Val Phe Ala Ile Ser His Leu Lys Glu Leu Ser Glu
    210                 215                 220

Glu Lys Ile Gly Lys Asp Leu Ala Glu Gln Val Asn His Ala Leu Glu
225                 230                 235                 240
```

Leu Pro Leu His Arg Arg Thr Gln Arg Leu Glu Ala Val Trp Ser Ile
            245                 250                 255

Glu Ala Tyr Arg Lys Lys Glu Asp Ala Asp Gln Val Leu Leu Glu Leu
        260                 265                 270

Ala Ile Leu Asp Tyr Asn Met Ile Gln Ser Val Tyr Gln Arg Asp Leu
    275                 280                 285

Arg Glu Thr Ser Arg Trp Trp Arg Arg Val Gly Leu Ala Thr Lys Leu
290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asp Asp Leu Pro Asp Tyr Met Lys Leu Cys Phe Leu
    370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
            420                 425                 430

Pro Thr Phe Asp Glu Tyr Phe Gly Asn Ala Trp Lys Ser Ser Ser Gly
        435                 440                 445

Pro Leu Gln Leu Val Phe Ala Tyr Phe Ala Val Val Gln Asn Ile Lys
    450                 455                 460

Lys Glu Glu Ile Asp Asn Leu Gln Lys Tyr His Asp Ile Ile Ser Arg
465                 470                 475                 480

Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
            500                 505                 510

Thr Lys Gly Ile Ser Glu Glu Leu Ala Thr Glu Ser Val Met Asn Leu
        515                 520                 525

Ile Asp Glu Thr Trp Lys Lys Met Asn Lys Glu Lys Leu Gly Gly Ser
    530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
        595

<210> SEQ ID NO 20
<211> LENGTH: 608
<212> TYPE: PRT
<213> ORGANISM: Pueraria montana
<220> FEATURE:
<223> OTHER INFORMATION: Pueraria montana var. lobata kudzu vine
      isoprene synthase (kIspS)

<400> SEQUENCE: 20

```
Met Ala Thr Asn Leu Leu Cys Leu Ser Asn Lys Leu Ser Pro Thr
1               5                   10                  15

Pro Thr Pro Ser Thr Arg Phe Pro Gln Ser Lys Asn Phe Ile Thr Gln
            20                  25                  30

Lys Thr Ser Leu Ala Asn Pro Lys Pro Trp Arg Val Ile Cys Ala Thr
        35                  40                      45

Ser Ser Gln Phe Thr Gln Ile Thr Glu His Asn Ser Arg Arg Ser Ala
    50                  55                  60

Asn Tyr Gln Pro Asn Leu Trp Asn Phe Glu Phe Leu Gln Ser Leu Glu
65              70                  75                      80

Asn Asp Leu Lys Val Glu Lys Leu Glu Glu Lys Ala Thr Lys Leu Glu
                85                  90                  95

Glu Glu Val Arg Cys Met Ile Asn Arg Val Asp Thr Gln Pro Leu Ser
            100                 105             110

Leu Leu Glu Leu Ile Asp Asp Val Gln Arg Leu Gly Leu Thr Tyr Lys
        115                 120             125

Phe Glu Lys Asp Ile Ile Lys Ala Leu Glu Asn Ile Val Leu Leu Asp
130             135                 140

Glu Asn Lys Lys Asn Lys Ser Asp Leu His Ala Thr Ala Leu Ser Phe
145                 150             155                 160

Arg Leu Leu Arg Gln His Gly Phe Glu Val Ser Gln Asp Val Phe Glu
            165                 170             175

Arg Phe Lys Asp Lys Glu Gly Gly Phe Ser Gly Glu Leu Lys Gly Asp
            180                 185             190

Val Gln Gly Leu Leu Ser Leu Tyr Glu Ala Ser Tyr Leu Gly Phe Glu
        195                 200             205

Gly Glu Asn Leu Leu Glu Glu Ala Arg Thr Phe Ser Ile Thr His Leu
        210                 215             220

Lys Asn Asn Leu Lys Glu Gly Ile Asn Thr Lys Val Ala Glu Gln Val
225                 230             235                 240

Ser His Ala Leu Glu Leu Pro Tyr His Gln Arg Leu His Arg Leu Glu
            245                 250             255

Ala Arg Trp Phe Leu Asp Lys Tyr Glu Pro Lys Glu Pro His His Gln
            260                 265             270

Leu Leu Leu Glu Leu Ala Lys Leu Asp Phe Asn Met Val Gln Thr Leu
        275                 280             285

His Gln Lys Glu Leu Gln Asp Leu Ser Arg Trp Trp Thr Glu Met Gly
        290                 295             300

Leu Ala Ser Lys Leu Asp Phe Val Arg Asp Arg Leu Met Glu Val Tyr
305             310             315                 320

Phe Trp Ala Leu Gly Met Ala Pro Asp Pro Gln Phe Gly Glu Cys Arg
            325                 330             335

Lys Ala Val Thr Lys Met Phe Gly Leu Val Thr Ile Ile Asp Asp Val
            340                 345             350

Tyr Asp Val Tyr Gly Thr Leu Asp Glu Leu Gln Leu Phe Thr Asp Ala
        355                 360             365

Val Glu Arg Trp Asp Val Asn Ala Ile Asn Thr Leu Pro Asp Tyr Met
370                 375             380

Lys Leu Cys Phe Leu Ala Leu Tyr Asn Thr Val Asn Asp Thr Ser Tyr
385             390                 395                 400

Ser Ile Leu Lys Glu Lys Gly His Asn Asn Leu Ser Tyr Leu Thr Lys
            405                 410             415
```

-continued

```
Ser Trp Arg Glu Leu Cys Lys Ala Phe Leu Gln Glu Ala Lys Trp Ser
            420                 425                 430

Asn Asn Lys Ile Ile Pro Ala Phe Ser Lys Tyr Leu Glu Asn Ala Ser
        435                 440                 445

Val Ser Ser Ser Gly Val Ala Leu Leu Ala Pro Ser Tyr Phe Ser Val
    450                 455                 460

Cys Gln Gln Gln Glu Asp Ile Ser Asp His Ala Leu Arg Ser Leu Thr
465                 470                 475                 480

Asp Phe His Gly Leu Val Arg Ser Ser Cys Val Ile Phe Arg Leu Cys
            485                 490                 495

Asn Asp Leu Ala Thr Ser Ala Ala Glu Leu Glu Arg Gly Glu Thr Thr
            500                 505                 510

Asn Ser Ile Ile Ser Tyr Met His Glu Asn Asp Gly Thr Ser Glu Glu
        515                 520                 525

Gln Ala Arg Glu Glu Leu Arg Lys Leu Ile Asp Ala Glu Trp Lys Lys
        530                 535                 540

Met Asn Arg Glu Arg Val Ser Asp Ser Thr Leu Leu Pro Lys Ala Phe
545                 550                 555                 560

Met Glu Ile Ala Val Asn Met Ala Arg Val Ser His Cys Thr Tyr Gln
            565                 570                 575

Tyr Gly Asp Gly Leu Gly Arg Pro Asp Tyr Ala Thr Glu Asn Arg Ile
            580                 585                 590

Lys Leu Leu Leu Ile Asp Pro Phe Pro Ile Asn Gln Leu Met Tyr Val
        595                 600                 605
```